(12) United States Patent
Huang et al.

(10) Patent No.: US 9,084,779 B2
(45) Date of Patent: Jul. 21, 2015

(54) CONJUGATES OF NITROIMIDAZOLES AND THEIR USE AS CHEMOTHERAPEUTIC AGENTS

(75) Inventors: Ru Chih C. Huang, Baltimore, MD (US); David Edward Mold, Baltimore, MD (US); Jih Ru Hwu, Hsinchu (CN); Ming Hua Hsu, Tucheng (CN); Szu Chun Wu, Hsinchu (CN)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/122,312

(22) PCT Filed: May 30, 2012

(86) PCT No.: PCT/US2012/039959
§ 371 (c)(1),
(2), (4) Date: Jan. 29, 2014

(87) PCT Pub. No.: WO2012/166778
PCT Pub. Date: Dec. 6, 2012

(65) Prior Publication Data
US 2014/0186266 A1  Jul. 3, 2014

Related U.S. Application Data

(60) Provisional application No. 61/491,535, filed on May 31, 2011.

(51) Int. Cl.
| | |
|---|---|
| A61K 31/4164 | (2006.01) |
| A61K 45/06 | (2006.01) |
| C07D 233/94 | (2006.01) |
| C07D 233/91 | (2006.01) |
| C07D 233/60 | (2006.01) |

(52) U.S. Cl.
CPC ............. *A61K 31/4164* (2013.01); *A61K 45/06* (2013.01); *C07D 233/60* (2013.01); *C07D 233/91* (2013.01); *C07D 233/94* (2013.01)

(58) Field of Classification Search
CPC ........................ A61K 31/4164; C07D 233/94
USPC .............. 548/327.5, 330.1; 424/9.1; 514/398
See application file for complete search history.

(56) References Cited

U.S. PATENT DOCUMENTS

| | | | |
|---|---|---|---|
| 7,741,357 B1 | 6/2010 | Huang et al. | |
| 8,232,277 B2 * | 7/2012 | Chen et al. | 514/252.11 |
| 8,420,692 B1 * | 4/2013 | Huang et al. | 514/408 |
| 2005/0267208 A1 | 12/2005 | Huang et al. | |
| 2008/0207532 A1 | 8/2008 | Huang et al. | |
| 2009/0306070 A1 | 12/2009 | Heller et al. | |

OTHER PUBLICATIONS

Mak, et al., "Tetra-O-methyl nordihydroguaiaretic acid inhibits growth and induces death of leukemia cells independent of Cdc2 and survivin", Leukemia & Lymphoma, (2007) vol. 48, No. 4, pp. 774-785, ISSN 1042-8194.

* cited by examiner

*Primary Examiner* — Joseph Kosack
*Assistant Examiner* — Amanda L Aguirre
(74) *Attorney, Agent, or Firm* — Johns Hopkins Technology Transfer

(57) ABSTRACT

Novel compounds which are derivatives of tetra-O-methyl nordihydroguaiaretic acid (NDGA), as well as pharmaceutically acceptable salts, solvates, and stereoisomers thereof are provided. These NDGA derivatives have a nitroimidazole moiety and these derivatives show preferential toxicity to hypoxic cells as hypoxic cytotoxins. Their cytotoxicity toward hypoxic cells is a result of abstraction of hydrogen from target molecules by free radicals formed in the reduction of the nitro group. This makes the disclosed compounds an effective anti cancer drug because hypoxic cells are generally considered to be more resistant to anti cancer drugs than normal cells. Pharmaceutical compositions comprising such compounds, as well as methods of use, and treatment for cancers, including hepatocellular carcinoma, breast cancer and prostate cancer, are also provided.

27 Claims, 13 Drawing Sheets

Compound 7c

DMSO

40 µM M3N

40 µM M3N-PEG-2NI

Control Group

Treated Group

Control Group Livers

Treated Group Livers

No Antibody

Hydroxyprobe

M3N

2NI-PEG-M3N

Adjacent   Tumor

CONJUGATES OF NITROIMIDAZOLES AND THEIR USE AS CHEMOTHERAPEUTIC AGENTS

CROSS-REFERENCE TO RELATED APPLICATIONS

This application is a 35 U.S.C. §371 U.S. national entry of International Application PCT/US2012/039959 having an international filing date of May 30, 2012, which claims the benefit of U.S. Provisional Application No. 61/491,535 filed May 31, 2011, the content of each of the aforementioned applications is herein incorporated by reference in their entirety.

BACKGROUND OF THE INVENTION

Hepatocellular carcinoma (HCC) is a major global health problem with >626,000 new cases per year worldwide. In North America, Asia, and Europe it is the third highest cause of cancer-related death, behind lung and colon cancer. A rise in the incidence and mortality of HCC has been observed in most industrialized nations over the past three decades. It probably reflects the increasing prevalence of hepatitis C virus infection in these countries. In the West, the disease is diagnosed at early stages in 30-40% of all patients and is amenable to potentially curative treatments, such as surgical therapies and locoregional procedures. Nevertheless, HCC remains a poorly treated cancer which afflicts more than half million people each year with survival rates of only 23% and <5% at 1 and 5 years, respectively. One reason for the high mortality rate is that treatment options are limited with few chemotherapeutic regimens currently approved for the treatment of unresectable HCC.

HCC is developed through cirrhosis brought on by chronic liver injury. This chronic injury results in fibrogenesis that damages the normal liver circulatory system and leads to the shortage of blood perfusion and oxygen delivery in the liver. Moreover, in tumor tissues, a high rate of cell proliferation in the tumor cells as well as abnormalities of structure and function associated with tumor vessels increases the need for oxygen. Through the activation of hypoxia inducible factor-1, hypoxia enhances proliferation, angiogenesis, metastasis, chemo- and radioresistance of HCC; it also suppresses cellular differentiation and apoptosis. Treatment of HCC by transarterial embolization also contributes to angiogenesis via hypoxia induction. Since angiogenesis plays an important role in recurrence of HCC after surgical resection, hypoxia targeting agents are becoming important tools in combinational therapy of this disease.

Nordihydroguaiaretic acid (NDGA, 1, FIG. 1) is a lipoxygenase inhibitor and anti-oxidation agent isolated from a desert medicinal plant, the Creosote bush (*Larrea tridentate*). In 2005, it was reported that tetra-O-methyl nordihydroguaiaretic acid (2, FIG. 1) can suppress the growth of a variety of mouse and human tumor cells as well as human tumor explants in nude mice. The development of this compound was prompted by the earlier discovery of naturally occurring 3-O-methyl nordihydroguaiaretic acid, which can inhibit HIV-1 viral replication by inhibiting the binding of transcription factor Sp1 to its cognate binding sites on the HIV long-terminal repeat promoter. The tetra-O-methylated NDGA derivative was subsequently synthesized and found to have similar Sp1 inhibitory activity.

In hypoxic cells, nitroimidazoles undergo a series of enzymic reductions, mediated by nitroreductase enzymes, and followed by ring fragmentation. Reactive radicals are thus generated, which then irreversibly bind to the cellular components. After the drugs enter the cell by passive diffusion, reduction enables more drugs to accumulate in the cell by a favorable concentration gradient as reduction proceeds intracellularly. In normoxic cells, the presence of oxygen prevents the enzymic reduction of nitroimidazole, and hence no binding occurs. In addition, nitroimidazoles show preferential toxicity to hypoxic cells as hypoxic cytotoxins. Their cytotoxicity toward hypoxic cells is a result of abstraction of hydrogen from target molecules by free radicals formed in the reduction of the nitro group.

There still exists an unmet need for novel nitroimidazole compounds that are useful for treating HCC and other cancers.

SUMMARY OF THE INVENTION

To enhance the effectiveness of tetra-O-methyl NDGA by targeting it towards hypoxic cancer cells, molecules were designed which incorporate tri-O-methyl NDGA (M3N) with a nitroimidazole moiety. To improve the water solubility, the nitroimidazole moiety was also tethered to NDGA with a water soluble polymer.

In accordance with an embodiment, the present invention provides a compound of Formula I:

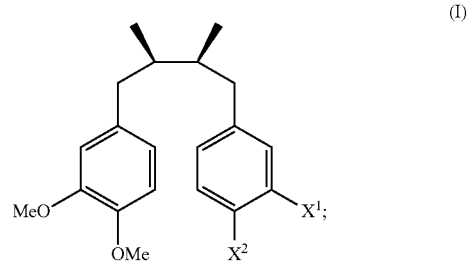

wherein $X^1$ and $X^2$ cannot be the same and are selected from the group consisting of H, OMe, and a nitroimidazole moiety of Formula Ia:

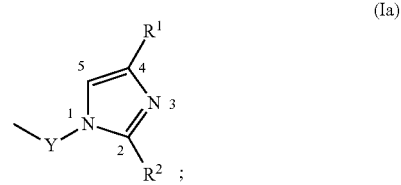

with the proviso that one of $X^1$ and $X^2$ must be the nitroimidazole moiety of Formula Ia; wherein $R^1$ and $R^2$ are the same or different, and are each selected from the group consisting of H and electron withdrawing groups; and wherein Y is a linking group consisting of a water soluble polymer having n subunits, and wherein the polymer is selected from the group consisting of polyethylene glycol, polyvinyl alcohol, polycaprolactone, polypropylene glycol, polyethyloxazoline, poly-L-lactic acid and related polymers and isomers thereof.

In accordance with another embodiment, the present invention provides a compound of Formula II:

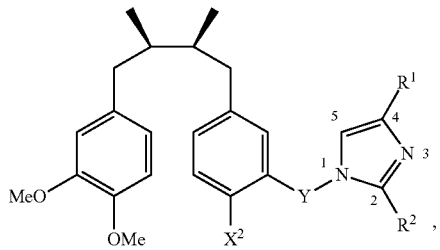

(II)

wherein $R^1$ and $R^2$ are the same or different, and are each selected from the group consisting of H and electron withdrawing groups; and wherein Y is a linking group consisting of a water soluble polymer having n subunits, and wherein the polymer is selected from the group consisting of polyethylene glycol, polyvinyl alcohol, polycaprolactone, polypropylene glycol, polyethyloxazoline, and poly-L-lactic acid and related polymers and isomers thereof.

In accordance with an embodiment, the present invention provides a compound, salt, solvate, or stereoisomer of Formula I or II, wherein the compound is a compound of Formula (III):

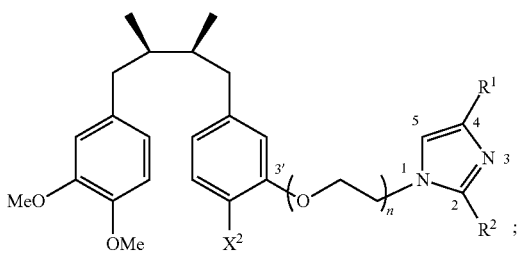

(III)

wherein Y is a polyethylene glycol moiety; n is 1-10; and wherein $R^1$ and $R^2$ are different, and are each selected from the group consisting of H and $NO_2$.

In accordance with an embodiment, the present invention provides a compound, salt, solvate, or stereoisomer of Formula I, wherein the compound is a compound of Formula (IV):

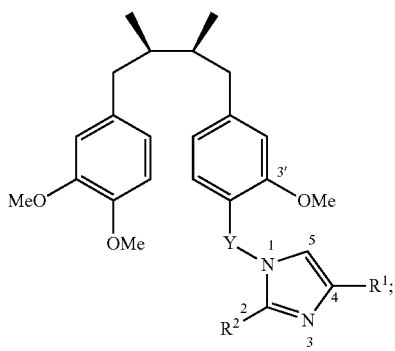

(IV)

wherein $R^1$ and $R^2$ are the same or different, and are each selected from the group consisting of H and electron withdrawing groups; and wherein Y is a linking group consisting of a water soluble polymer having n subunits, and wherein the polymer is selected from the group consisting of polyethylene glycol, polyvinyl alcohol, polycaprolactone, polypropylene glycol, polyethyloxazoline, and poly-L-lactic acid and related polymers and isomers thereof.

In accordance with an embodiment, the present invention provides a compound, salt, solvate, or stereoisomer of Formula I or IV, wherein the compound is a compound of Formula (V):

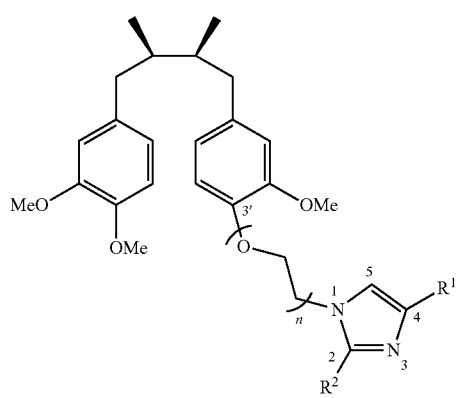

(V)

wherein Y is a polyethylene glycol moiety; n is 1-10; and wherein $R^1$ and $R^2$ are different, and are each selected from the group consisting of H and $NO_2$.

In accordance with an embodiment, the present invention provides a pharmaceutical composition comprising a compound, salt, solvate, or stereoisomer of any of the above described compounds, and a pharmaceutically acceptable carrier.

In accordance with another embodiment, the present invention provides pharmaceutical composition comprising a compound, salt, solvate, or stereoisomer of any of the above described compounds, at least one additional therapeutic agent, and a pharmaceutically acceptable carrier.

In accordance with an embodiment, the present invention provides a method of treating or preventing cancer in a subject comprising administering to the subject an effective amount of a compound, salt, solvate, or stereoisomer of any of the above described compounds.

In accordance with an embodiment, the present invention provides a compound, salt, solvate, or stereoisomer of any of the above described compounds, for use in preparing a medicament.

DETAILED DESCRIPTION OF THE INVENTION

Figure 1:
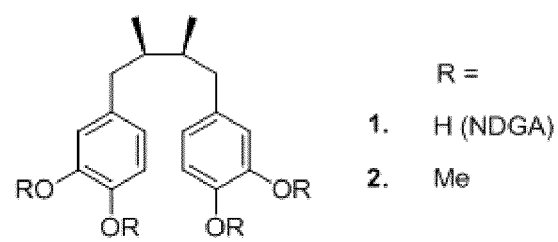
FIG. 1 depicts the chemical structure of nordihydroguaiaretic acid (NDGA, 1) and tetra-O-methyl nordihydroguaiaretic acid (2).

In accordance with one or more embodiments of the present invention, the inventors have created a series of molecules wherein a nitroimidazole group is attached to the M3N molecule to take advantage of the fact that hypoxic tumor cells will create an environment without oxygen. Without oxygen, the enzymatic reduction of the nitroimidazole group can occur and nitroimidazoles undergo a series of enzymatic reductions, mediated by nitroreductase enzymes. This results in the irreversible binding of the reactive radicals generated and promotes the accumulation of the drug and reactive radicals at the tumor site. In normoxic cells, the presence of oxygen prevents the enzymatic reduction of nitroimidazole, and hence no binding occurs. In addition, nitroimidazole derivatives show preferential toxicity to hypoxic cells and act as hypoxic cytotoxins. Their cytotoxicity toward hypoxic cells is a result of abstraction of hydrogen from target molecules by free radicals formed in the reduction of the nitro group. This makes M3N a more effective anti cancer drug because hypoxic cells are generally considered to be more resistant to anti cancer drugs than normal cells. Hypoxic cells are also considered to be resistant to most anticancer drugs for several reasons. First, hypoxic cells are distant from blood vessels and, as a result, are not adequately exposed to some types of anticancer drugs and second, the action of some anticancer agents (for example, bleomycin) resembles that of radiation in that oxygen increases the cytotoxicity of the DNA lesions they cause.

In accordance with an embodiment, the present invention provides a compound of Formula I:

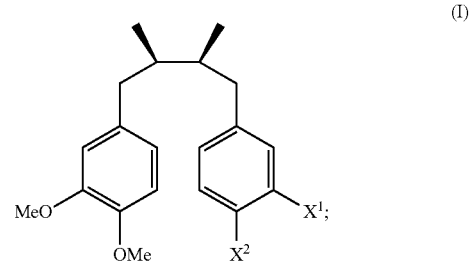

wherein $X^1$ and $X^2$ cannot be the same and are selected from the group consisting of H, OMe, and a nitroimidazole moiety of Formula Ia:

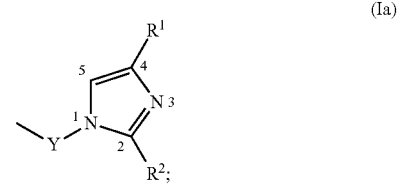

with the proviso that one of $X^1$ and $X^2$ must be the nitroimidazole moiety of Formula Ia; wherein $R^1$ and $R^2$ are the same or different, and are each selected from the group consisting of H and electron withdrawing groups; and wherein Y is a linking group consisting of a water soluble polymer having n subunits, and wherein the polymer is selected from the group consisting of polyethylene glycol, polyvinyl alcohol, polycaprolactone, polypropylene glycol, polyethyloxazoline, and poly-L-lactic acid and related polymers and isomers thereof.

In accordance with another embodiment, the present invention provides a compound of Formula II:

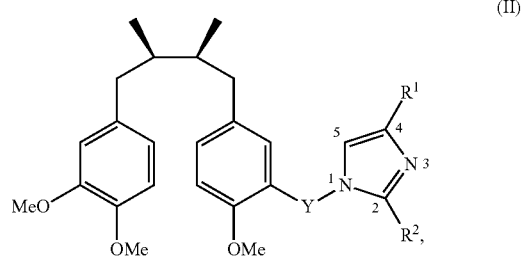

wherein $R^1$ and $R^2$ are the same or different, and are each selected from the group consisting of H and electron withdrawing groups; and wherein Y is a linking group consisting of a water soluble polymer having n subunits, and wherein the polymer is selected from the group consisting of polyethylene glycol, polyvinyl alcohol, polycaprolactone, polypropylene glycol, polyethyloxazoline, and poly-L-lactic acid and related polymers and isomers thereof.

In a further embodiment, the present invention provides a compound, salt, solvate, or stereoisomer of either of Formula I or II, wherein the electron withdrawing group is selected from the group consisting of SCN, $N_3$, CN, $SO_3H$, $B(OH)_2$, $PO(OH)_2$, $SO_2NHOH$, $SO_2NH_2$, CONHOH, $NO_2$, CHO, COOR", COR", NR"$_3$+, wherein R" is H or $C_1$-$C_6$ alkyl, and $CZ_3$, wherein Z is F, Cl, or Br.

In accordance with an embodiment, the present invention provides a compound, salt, solvate, or stereoisomer of Formula I or II, wherein the compound is a compound of Formula (III):

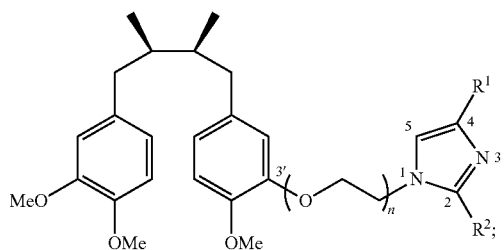

wherein Y is a polyethylene glycol moiety; n is 1-10; and wherein $R^1$ and $R^2$ are different, and are each selected from the group consisting of H and $NO_2$.

In another embodiment, the present invention provides a compound, salt, solvate, or stereoisomer of Formula III, wherein n=1.

In a further embodiment, the present invention provides a compound, salt, solvate, or stereoisomer of Formula III, wherein n=4.

In an embodiment, the present invention provides a compound, salt, solvate, or stereoisomer of Formula I, II, or III, wherein the compound is one of the following:

Compound 7a

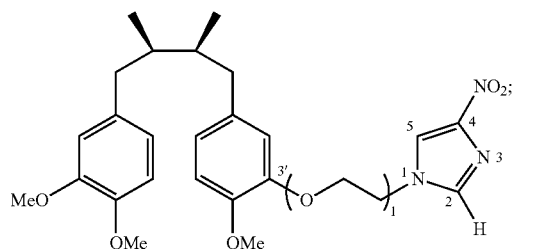

Compound 7b

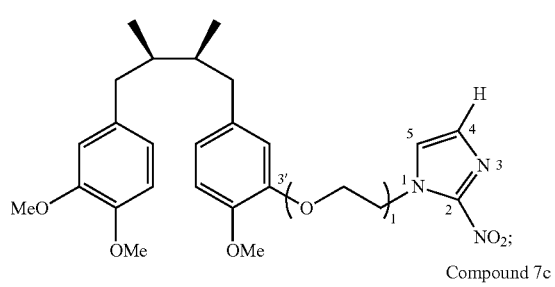

Compound 7c

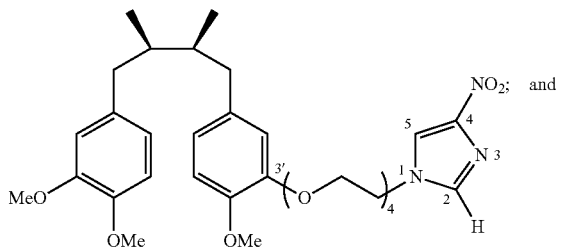

and

Compound 7d

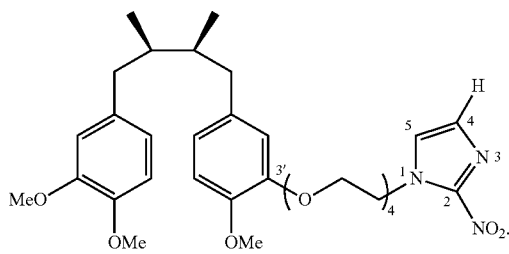

In accordance with an embodiment, the present invention provides a compound, salt, solvate, or stereoisomer of Formula I, wherein the compound is a compound of Formula (IV):

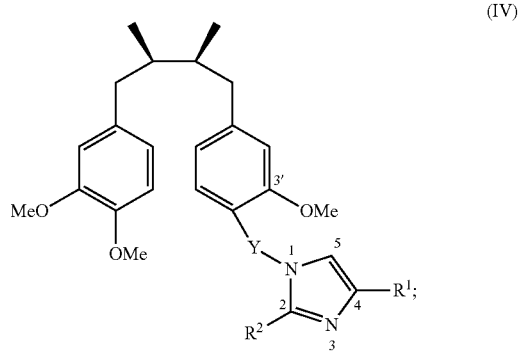

wherein $R^1$ and $R^2$ are the same or different, and are each selected from the group consisting of H and electron withdrawing groups; and wherein Y is a linking group consisting of a water soluble polymer having n subunits, and wherein the polymer is selected from the group consisting of polyethylene glycol, polyvinyl alcohol, polycaprolactone, polypropylene glycol, polyethyloxazoline, and poly-L-lactic acid and related polymers and isomers thereof.

In a further embodiment, the present invention provides a compound, salt, solvate, or stereoisomer of either of Formula IV, wherein the electron withdrawing group is selected from the group consisting of SCN, $N_3$, CN, $SO_3H$, $B(OH)_2$, $PO(OH)_2$, $SO_2NHOH$, $SO_2NH_2$, CONHOH, $NO_2$, CHO, COOR", COR", NR"$_3$+, wherein R" is H or $C_1$-$C_6$ alkyl, and $CZ_3$, wherein Z is F, Cl, or Br.

In another embodiment, the present invention provides a compound, salt, solvate, or stereoisomer of Formula IV, wherein n=1.

In a further embodiment, the present invention provides a compound, salt, solvate, or stereoisomer of Formula IV, wherein n=4.

In accordance with an embodiment, the present invention provides a compound, salt, solvate, or stereoisomer of Formula I or IV, wherein the compound is a compound of Formula (V):

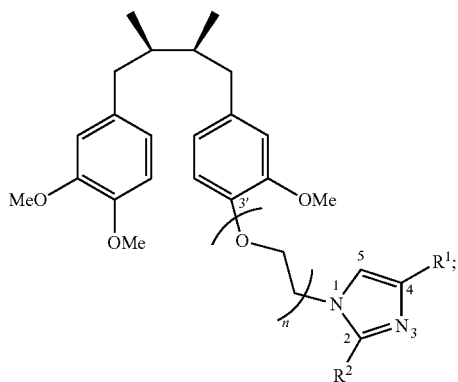

(V)

wherein Y is a polyethylene glycol moiety; n is 1-10; and wherein $R^1$ and $R^2$ are different, and are each selected from the group consisting of H and $NO_2$.

In another embodiment, the present invention provides a compound, salt, solvate, or stereoisomer of Formula V, wherein n=1.

In a further embodiment, the present invention provides a compound, salt, solvate, or stereoisomer of Formula V, wherein n=4.

In an embodiment, the present invention provides a compound, salt, solvate, or stereoisomer of Formula I, IV, or V, wherein the compound is one of the following:

Compound 10a

Compound 10b

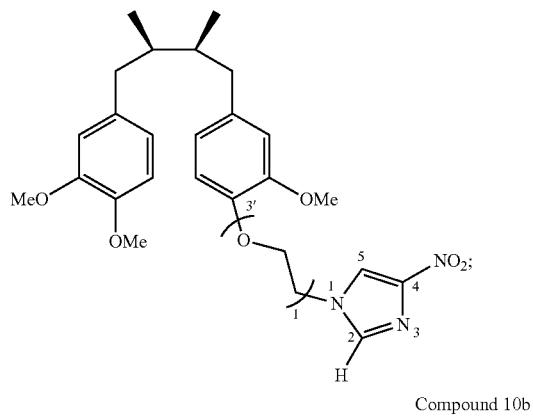

Compound 10c

Compound 10d

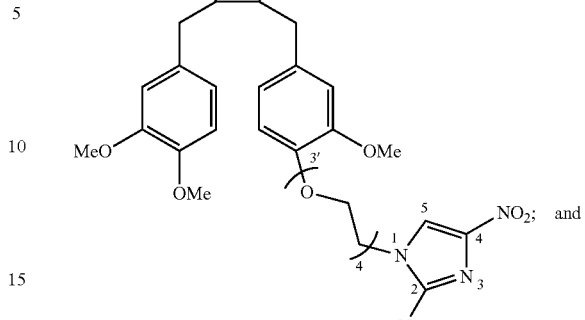

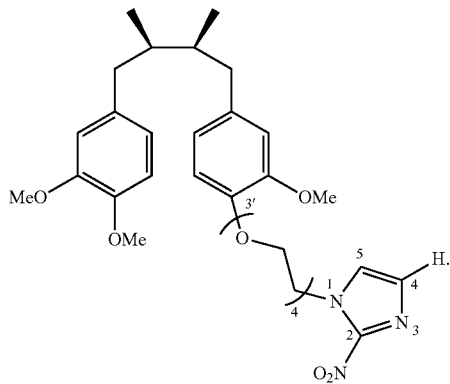

In an embodiment, the present invention provides a pharmaceutical composition comprising a compound, salt, solvate, or stereoisomer of any of the above described compounds, and a pharmaceutically acceptable carrier.

In another embodiment, the present invention provides pharmaceutical composition comprising a compound, salt, solvate, or stereoisomer of any of the above described compounds, at least one additional therapeutic agent, and a pharmaceutically acceptable carrier.

Included within the compounds of the present invention are the tautomeric forms of the disclosed compounds, isomeric forms including diastereoisomers, and the pharmaceutically-acceptable salts thereof. The term "pharmaceutically acceptable salts" embraces salts commonly used to form alkali metal salts and to form addition salts of free acids or free bases. Examples of acids which may be employed to form pharmaceutically acceptable acid addition salts include such inorganic acids as hydrochloric acid, sulphuric acid and phosphoric acid, and such organic acids as maleic acid, succinic acid and citric acid. Other pharmaceutically acceptable salts include salts with alkali metals or alkaline earth metals, such as sodium, potassium, calcium and magnesium, or with organic bases, such as dicyclohexylamine. Suitable pharmaceutically acceptable salts of the compounds of the present invention include, for example, acid addition salts which may, for example, be formed by mixing a solution of the compound according to the invention with a solution of a pharmaceutically acceptable acid, such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. All of these salts may be prepared by conventional means by reacting, for example, the appropriate acid or base with the corresponding compounds of the present invention.

Salts formed from free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For use in medicines, the salts of the compounds of the present invention should be pharmaceutically acceptable salts. Other salts may, however, be useful in the preparation of the compounds according to the invention or of their pharmaceutically acceptable salts.

In addition, embodiments of the invention include hydrates of the compounds of the present invention. The term "hydrate" includes but is not limited to hemihydrate, monohydrate, dihydrate, trihydrate and the like. Hydrates of the compounds of the present invention may be prepared by contacting the compounds with water under suitable conditions to produce the hydrate of choice.

With respect to the pharmaceutical compositions described herein, the carrier can be any of those conventionally used, and is limited only by physico-chemical considerations, such as solubility and lack of reactivity with the active compound(s), and by the route of administration. The carriers described herein, for example, vehicles, adjuvants, excipients, and diluents, are well-known to those skilled in the art and are readily available to the public. It is preferred that the carrier be one which is chemically inert to the active agent(s), and one which has little or no detrimental side effects or toxicity under the conditions of use. Examples of the carriers include solid compositions such as solid-state carriers or latex beads.

Solid carriers or diluents include, but are not limited to, gums, starches (e.g., corn starch, pregelatinized starch), sugars (e.g., lactose, mannitol, sucrose, dextrose), cellulosic materials (e.g., microcrystalline cellulose), acrylates (e.g., polymethylacrylate), calcium carbonate, magnesium oxide, talc, or mixtures thereof.

The choice of carrier will be determined, in part, by the particular pharmaceutical composition, as well as by the particular method used to administer the composition. Accordingly, there are a variety of suitable formulations of the pharmaceutical composition of the invention.

It will be understood to those of skill in the art that the term "therapeutic agent" is any agent capable of affecting the structure or function of the body of a subject or is an agent useful for the treatment or modulation of a disease or condition in a subject suffering therefrom. Examples of therapeutic agents can include any drugs known in the art for treatment of disease indications. A particular example of a therapeutic agent is a chemotherapeutic agent.

The term "chemotherapeutic agent" as well as words stemming therefrom, as used herein, generally includes pharmaceutically or therapeutically active compounds that work by interfering with DNA synthesis or function in cancer cells. Based on their chemical action at a cellular level, chemotherapeutic agents can be classified as cell-cycle specific agents (effective during certain phases of cell cycle) and cell-cycle nonspecific agents (effective during all phases of cell cycle). Without being limited to any particular example, examples of chemotherapeutic agents can include alkylating agents, angiogenesis inhibitors, aromatase inhibitors, antimetabolites, anthracyclines, antitumor antibiotics, monoclonal antibodies, platinums, topoisomerase inhibitors, and plant alkaloids. Further examples of chemotherapeutic agents include asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

In accordance with an embodiment, the additional therapeutic agent is an anticancer or chemotherapeutic agent selected from the group consisting of, antimitotics, antineoplastics, antimetabolites, and alkylating agents.

In accordance with another embodiment, the additional therapeutic agent is an imaging agent, including, for example, radionuclides and fluorescent dyes.

In accordance with an embodiment, the present invention provides a method of treating or preventing cancer in a subject comprising administering to the subject an effective amount of a compound, salt, solvate, or stereoisomer of any of the above described compounds.

In accordance with another embodiment, the cancer being treated can be any cancer where the disease presents as one or more solid tumors. Examples of such cancers include, alveolar rhabdomyosarcoma, bone cancer, brain cancer, breast cancer, cancer of the anus, anal canal, or anorectum, cancer of the eye, cancer of the intrahepatic bile duct, cancer of the neck, gallbladder, or pleura, cancer of the nose, nasal cavity, or middle ear, cancer of the oral cavity, cancer of the vulva, colon cancer, esophageal cancer, cervical cancer, gastrointestinal carcinoid tumor, hypopharynx cancer, kidney cancer, larynx cancer, hepatocellular carcinoma, lung cancer, malignant mesothelioma, melanoma, multiple myeloma, nasopharynx cancer, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer. Preferably, the cancer is hepatocellular carcinoma, breast cancer and pancreatic cancer, as well as any cancer known to form solid tumors.

In accordance with an embodiment, the present invention provides a compound, salt, solvate, or stereoisomer of any of the above described compounds, for use in preparing a medicament, preferably a medicament for use in treating cancer, and more preferably, for use in treating hepatocellular carcinoma, breast cancer and pancreatic cancer in a subject.

For purposes of the invention, the amount or dose of the compositions of the present invention that is administered should be sufficient to effectively target the cell, or population of cells in vivo, such that cell apoptosis or death in the target cell or population of cells occurs in the subject over a reasonable time frame. The dose will be determined by the efficacy of the particular pharmaceutical formulation and the location of the target population of cells in the subject, as well as the body weight of the subject to be treated.

An active agent and a biologically active agent are used interchangeably herein to refer to a chemical or biological compound that induces a desired pharmacological and/or physiological effect, wherein the effect may be prophylactic or therapeutic. The terms also encompass pharmaceutically acceptable, pharmacologically active derivatives of those active agents specifically mentioned herein, including, but not limited to, salts, esters, amides, prodrugs, active metabolites, analogs and the like. When the terms "active agent," "pharmacologically active agent" and "drug" are used, then, it is to be understood that the invention includes the active agent per se, as well as pharmaceutically acceptable, pharmacologically active salts, esters, amides, prodrugs, metabolites, analogs etc.

The dose of the compositions of the present invention also will be determined by the existence, nature and extent of any adverse side effects that might accompany the administration of a particular composition. Typically, an attending physician will decide the dosage of the pharmaceutical composition with which to treat each individual subject, taking into consideration a variety of factors, such as age, body weight, general health, diet, sex, compound to be administered, route of administration, and the severity of the condition being treated. By way of example, and not intending to limit the invention, the dose of the pharmaceutical compositions of the present invention can be about 0.001 to about 1000 mg/kg body weight of the subject being treated, from about 0.01 to about 100 mg/kg body weight, from about 0.1 mg/kg to about 10 mg/kg, and from about 0.5 mg to about 5 mg/kg body weight. In another embodiment, the dose of the pharmaceutical compositions of the present invention can be at a concentration from about 100 nM to about 100 µM, preferably from about 1 µM to about 50 µM, more preferably from about 10 µM to about 30 µM.]

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

In an embodiment, the compounds of the present invention, or salts, solvates or stereoisomers thereof, provided herein are controlled release compositions, i.e., compositions in which the one or more compounds are released over a period of time after administration. Controlled or sustained release compositions include formulation in lipophilic depots (e.g., fatty acids, waxes, oils).

Pharmaceutically acceptable salts are art-recognized, and include relatively non-toxic, inorganic and organic acid addition salts of compositions of the present invention, including without limitation, therapeutic agents, excipients, other materials and the like. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. Examples of suitable inorganic bases for the formation of salts include the hydroxides, carbonates, and bicarbonates of ammonia, sodium, lithium, potassium, calcium, magnesium, aluminum, zinc and the like. Salts may also be formed with suitable organic bases, including those that are non-toxic and strong enough to form such salts. For purposes of illustration, the class of such organic bases may include mono-, di-, and trialkylamines, such as methylamine, dimethylamine, and triethylamine; mono-, di-, or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenthylamine; (trihydroxymethyl)aminoethane; and the like, see, for example, J. Pharm. Sci., 66: 1-19 (1977).

The "therapeutically effective amount" of the pharmaceutical compositions to be administered will be governed by such considerations, and can be the minimum amount necessary to prevent, ameliorate or treat a disorder of interest. As used herein, the term "effective amount" is an equivalent phrase refers to the amount of a therapy (e.g., a prophylactic or therapeutic agent), which is sufficient to reduce the severity and/or duration of a disease, ameliorate one or more symptoms thereof, prevent the advancement of a disease or cause regression of a disease, or which is sufficient to result in the prevention of the development, recurrence, onset, or progression of a disease or one or more symptoms thereof, or enhance or improve the prophylactic and/or therapeutic effect(s) of another therapy (e.g., another therapeutic agent) useful for treating a disease, such as cancer.

In accordance with one or more embodiments, suitable hydrophilic polymers to serve as the linking moiety Y include, for example, synthetic polymers such as of polyethylene glycol, polyvinyl alcohol, polycaprolactone, polypropylene glycol, polyethyloxazoline, and poly-L-lactic acid and related polymers and isomers thereof

EXAMPLES

Chemistry. All reactions were carried out in oven-dried glassware (110° C.) under an atmosphere of nitrogen, unless indicated otherwise. Acetone, ethanol, ethyl acetate (EtOAc), and hexanes were purchased from Mallinckrodt Chemical Co. Ethyl acetate and hexanes were dried and distilled from $CaH_2$. Acetone and ethanol of HPLC grade were purchased from Mallinckrodt Chemical Co. and used without further purification. Potassium carbonate was purchased from Fisher Scientific. Trimethyl nordihydroguaiaretic acid and bis[2-(2-bromoethoxy)ethyl]ether were prepared according to the reported methods.

Melting points were obtained with a Fargo MP-2D melting point apparatus. Analytical thin layer chromatography was performed on precoated plates (silica gel 60 F-254), purchased from Merck Inc. Purification by gravity column chromatography was carried out by use of Merck Reagents Silica Gel 60 (particle size 0.063-0.200 mm, 70-230 mesh ASTM).

Infrared (IR) spectra were measured on a Perkin Elmer RX 1 FT-IR spectrometer. Absorption intensities are recorded by the following abbreviations: s, strong; m, medium; w, weak; br, broad. Ultraviolet (UV) spectra were measured on Jasco V-570 UV/VIS/NIR spectrophotometer. High-resolution mass spectra were obtained by means of a JEOL JMS-700 mass Spectrometer. Proton NMR spectra were obtained on a Varian Mercury-400 (400 MHz) spectrometer by use of chloroform-d as the solvent. Carbon-13 NMR spectra were performed on a Varian Mercury-400 (100 MHz) spectrometer by use of chloroform-d as the solvent. Carbon-13 chemical shifts are referenced to the center of the $CDCl_3$ triplet (677.0 ppm). Multiplicities are recorded by the following abbreviations: s, singlet; d, doublet; t, triplet; q, quartet; m, multiplet; J, coupling constant (Hz).

Anti-proliferative assay. The human hepatocellular carcinoma cell line Hep3B was purchased from American Type culture Collection (ATCC, Manassas, Va.). Dulbecco's Modified Eagle Medium (DMEM) and penicillin/streptomycin (P/S) were obtained from GIBCO Invitrogen. Fetal Bovine serum (FBS) was obtained from Thermo Scientific Hyclone. Dimethyl sulfoxide (DMSO-Hybri-Max) was purchased from Sigma-Aldrich Co. and the CellTiter 96 AQueous One Solution Cell Proliferation Assay (MTS) was acquired from Promega Corp. Hep3B cells were maintained in DMEM supplemented with 10% FBS and 1× P/S solution. Cultures were incubated at 37° C. in a 5% $CO_2$ atmosphere with 99% humidity. Stock solutions of test compounds were prepared in DMSO for use in the cell culture viability assays.

MTS tetrazolium cell proliferation assay. The viability of Hep3B cells exposed to the synthesized compounds was determined by the MTS assay. Briefly, Hep3B cells were plated in 96-well plates at a density of $3.0 \times 10^3$ cells/well and incubated for 24-h before treatment. At the initiation of treatment, the growth media was replaced with 200 μL of media containing increasing concentrations of the test compounds in triplicate wells. The final DMSO concentration in the media was 1.0% including the media added to the control wells minus the test compound. After a 72-hour incubation, 40 μL of MTS solution was added to each well and the plates were incubated for an additional 3.0 hours. The plates were then read at 490 nm on a Biotek Instruments PowerWave 200 microplate reader. For each experiment the percent growth inhibition relative to the control (no drug addition) was calculated and a dose inhibition curve was generated. The concentration of drug required to inhibit cell growth by 50% ($IC_{50}$) compared to the control cells was then determined by non-linear regression using PSI-Plot software (Poly Software International).

Hypoxia targeting assay. Hep3B cells, plated in 96-well plates at a density of $3.0 \times 10^3$ cells/well, were incubated overnight and then treated with the test compounds for 5.0 hours at under hypoxic (1% $O_2$) or normoxic (21% $O_2$) conditions. Exposure of cells to hypoxia was carried out in a PROOX C-Chamber with $O_2$ and $CO_2$ levels modulated by a PROOX Model C21 Controller (BioSpherix). At the end of the treatment period, the wells were washed with phosphate buffered saline (PBS) and fresh compound-free media was added. The cells were cultured for an additional 5 days under normoxic conditions and then assayed for cell proliferation using the MTS assay.

Additional cell culture, drug treatment and cell viability assays. HT29 human colorectal carcinoma cells, 786-0 human renal adenocarcinoma cells and Hep3B human hepatocellular carcinoma cells were obtained from ATCC and maintained in culture according to their recommendations. To obtain $IC_{50}$ values for the cytotoxic activity of M3N and M3N-PEG-2NI, cells were grown in the presence of increasing concentrations of drug in media containing 1% DMSO for 3 days under normoxic conditions. After the treatment period viability of the cells was determined with the MTT cell viability assay and dose response curves were generated using the calculated values of the percentage viable cells relative to the vehicle control.

For the further assessment of cell viability by plating efficiency, cells ($2 \times 10^6$ cells/100 mm dish) from the human colorectal carcinoma cell line HT29 were treated for 48 hours with 40 μM M3N, 40 μM M3N-PEG-2NI or the DMSO vehicle. At the end of the treatment period, the cells from each dish were released by trypsinization, diluted 10,000 fold and replated into new 100 mm dishes. Eight days later colonies were stained with 0.25% methylene blue in 50% ethanol Orthotopic Xenograft implantation of HT29 human colorectal carcinoma cells into nude mice. HT29 cells were grown in culture in McCoy's medium until sub-confluent. A single cell suspension of HT29 was then prepared in HBSS and $1 \times 10^7$ cells were injected subcutaneously into the flanks of four male T-cell deficient nude (Nu/Nu) mice. Subcutaneous tumors were allowed to grow for 14 days before harvesting and preparation for orthotopic implantation. The mice were euthanized and the subcutaneous tumors were removed using sterile technique. The tumors were divided into 3×3 mm pieces that were kept in phosphate buffered saline (PBS) on ice. T-cell deficient nude (NU/NU) mice (6 male, 5 female) were anesthetized by injecting 0.5 to 1.0 mL of Avertin (20 mM) intraperitoneally in PBS. The abdomen was prepped with 70% ethanol three times and a small nick was made in the skin. The abdominal wall musculature was grasped, lifted, and entered with a single blade of scissors. The single blade of the scissors was used to push the contents of the abdominal cavity away and the incision was extended 2-3 cm. The cecum was identified by its blind ending pouch and exteriorized. The cecum was isolated from the rest of the mouse using pre-cut, sterile gauze and kept moist with warm PBS. A figure of 8 stitches was placed onto the cecum using a 7-0 sized suture and the cecal wall was slightly damaged at the site where the HT29 tumor piece is to be implanted using forceps. An HT29 tumor piece was positioned on the cecum under the stitch and the stitch was then tied. The cecum was returned to the abdominal cavity. Using staples, the mouse abdominal wall musculature and skin was closed and the mouse was allowed to recover from anesthesia.

Figure 7:
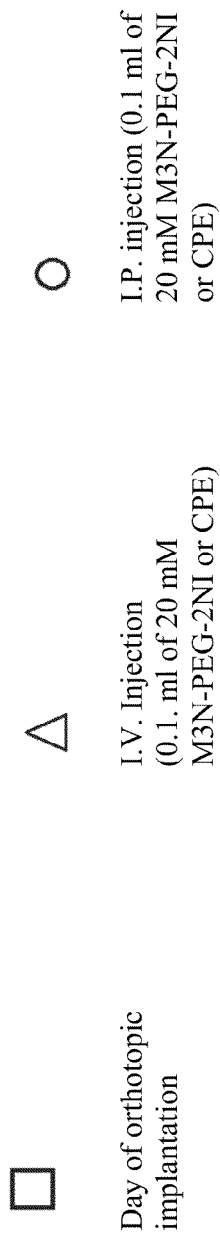
FIG. 7 shows the schedule and routes of 2NI-PEG-M3N administration to nude mice orthotopically explanted with human colorectal tumor fragments.

Systemic treatment with M3N-PEG-2NI (compound 7d). A 40 mM stock solution of M3N-PEG-2NI was prepared by dissolving 0.14 g of M3N-PEG-2NI (MW=616.3 g/mol) in 5.7 mL of CPE. Each day of treatment, 4 T-cell deficient nude mice (2 male, 2 female) bearing orthotopic HT29 tumor implants received 0.1 ml of 20 mM M3N-PEG-2NI via I.V. or I.P. injections. The remaining 4 T-cell deficient nude mice (2 male, 2 female) received 0.1 mL of CPE (FIG. 7) Body weight of mice was monitored every week, until significant body weight change occurred. Then, body weight was measured every other day until day 24. All 8 mice were euthanized on day 24. The mice were dissected and their major organs collected. Special attention was taken in examination of livers since liver metastasis is common in orthotopic colon cancer models.

Western blot analysis of 2-nitroimidazole induced protein adducts in LNCaP cell cultures. Exponentially growing LNCaP human prostate cancer cells were treated with DMSO, 80 μM M3N-PEG-2NI or Hypoxyprobe-1 in standard media for 6 hours under normoxic conditions and then under hypoxic or normoxic conditions for additional 6 hours. Afterward the media was aspirated, the cells washed and ice cold RIPA lysis buffer was added and the cells lysed on ice for 15 minutes. The samples were centrifuged and the lysate collected. Cellular proteins in the extracts were analyzed for the presence of protein adducts using standard western blotting technique. The primary antibody was PAb2627 polyclonal antibody (1:200) directed against Hydroxyprobe-1 protein adducts. The secondary antibody was Anti-Rabbit HRP conjugate (1:2000). Detection was by chemiluminescence Immunofluorescence analysis of 2-nitroimidazole induced protein adducts in mouse tumor explants. Nude mice with subcutaneous LNCaP prostate cancer cell explants were administered Hydroxyprobe-1, M3N or M3N-PEG-2NI for three weeks by daily intravenous tail vein injection with an additional injection 3 hours prior to euthanization. Tumors were removed from the euthanized mice by dissection and incubated in 30% sucrose/PBS overnight at 4° C. Excess sucrose was removed and the tissue was incubated in 30% sucrose/PBS:OCT (1:1) for 1 hour at room temperature. Afterward the tissue was frozen in 100% OCT. Frozen sections of 7-14 µM were prepared and fixed in 4% PFA/PBS for 1 hour at room temperature. The sections were blocked overnight at 4° C. with 5% goat serum/PBS or at room temperature for 1 hour and then incubated with Hydroxyprobe-1 rabbit antiserum (1:200) overnight at 4° C. After three washes with PBS, the secondary antibody, mouse anti rabbit-FITC (1:1000) was added for 1 hour at room temperature. The sections were mounted using Vectashield and fluorescently imaged.

Example 1

Figure 2:
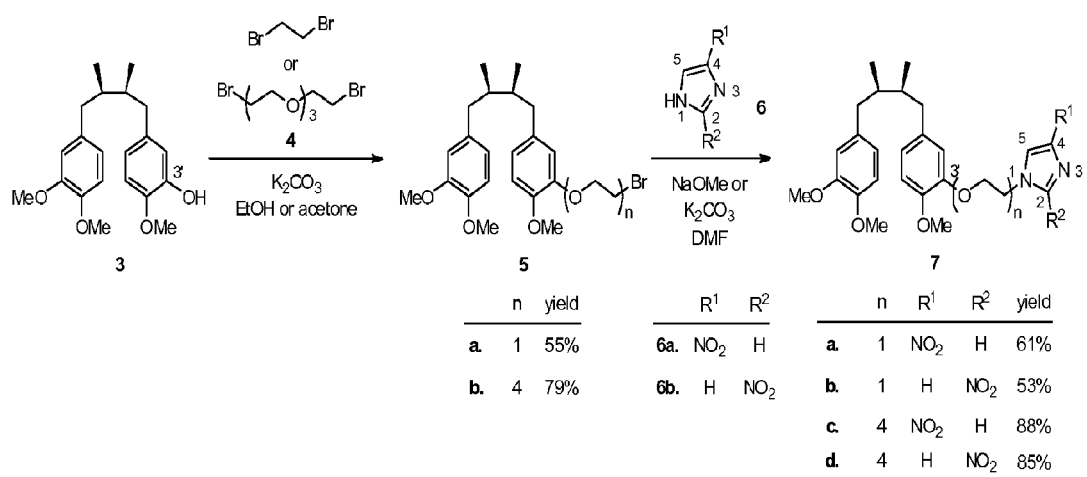
FIG. 2 depicts the synthetic scheme for synthesis of derivatives 7a-d from compound 3.

Using the method of Hwu et al. (*J. Med. Chem.* 1998, 41, 2994-3000), two isomeric trimethyl NDGA (±)-3 and (±)-8 were obtained in pure form as the starting materials for the syntheses of the conjugates 7 and 10 (see Scheme 1, FIG. 2). Treatment of 3 with 1,2-dibromoethane in the presence of potassium carbonate gave the corresponding NDGA bromide 5a. Regioisomeric 4- and 2-nitroimidazoles 6a and 6b are commercially available and were used respectively to couple with 5a under alkaline conditions. The desired NDGA-nitroimidazoles (±)-7a and (±)-7b were obtained in 61% and 53% yields, respectively. Given the same synthetic procedure by using bis[2-(2-bromoethoxy)ethyl]ether (4) to replace 1,2-dibromoethane, we produced PEG-containing conjugates 7c and 7d in higher yields (85-88%).

Figure 3:
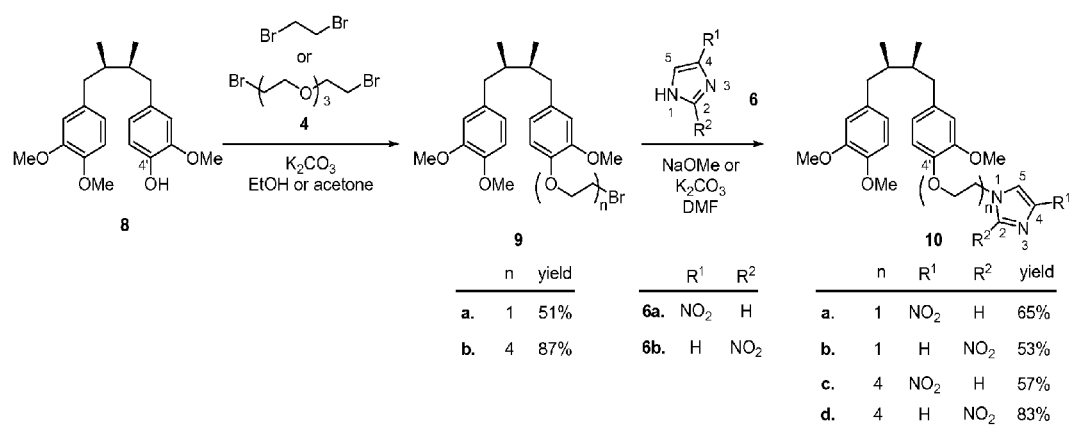
FIG. 3 depicts the synthetic scheme for synthesis of derivatives 10a-d from compound 8.

After the nitroimidazole moieties were tethered to the 3'-position of NDGA in conjugates 7a-d, the corresponding regioisomeric 4'-analogs were also obtained. Syntheses were started with the trimethyl NDGA (±)-8 with a free hydroxyl group at the 4'-position. As shown in Scheme 2 (FIG. 3), the desired 4'-tethered NDGA-nitroimidazole conjugates (±)-10a-d were generated via 9a,b in appealing yields.

Structures of these new NDGA derivatives 5a,b, 7a-d, 9a,b, and 10a-d were fully characterized by $^1$H NMR, $^{13}$C NMR, IR, and mass spectroscopic methods. For example, conjugate 7c exhibited three singlets at 3.78, 3.82, and 3.83 ppm in its $^1$H NMR spectrum for the three OCH$_3$ protons, individually. The six CHCH$_3$ protons in the two methyl groups of NDGA moiety showed an overlapped doublet with J=6.0 Hz at 0.80 ppm. The two characteristic CH=CNO$_2$ and NCH=N protons in the nitroimidazole unit appeared as two doublets with J=1.0 Hz at 7.46 and 7.87 ppm, respectively. The 14 OCH$_2$ protons in the PEG tether resonated at 3.61-4.12 pm as multiplets. In its $^{13}$C NMR spectrum, three peaks showed up at 120.17, 136.45, and 147.69 ppm for the C-5, C-2, and C-4 carbons in the imidazole nucleus, individually[27]. In its IR spectrum, two strong (i.e., 1516 and 1335 cm$^{-1}$) and one medium (i.e., 1541 cm$^{-1}$) absorption bands appeared for the NO$_2$ and C=C stretching vibrations, respectively. Its exact mass, measured by the FABMS technique, was determined as 615.3161, which is consistent with the theoretical value 615.3156. These data clearly indicate that the conjugate 7c possessed an NDGA moiety, a PEG tether, and a nitroimidazole unit.

Figure 4:
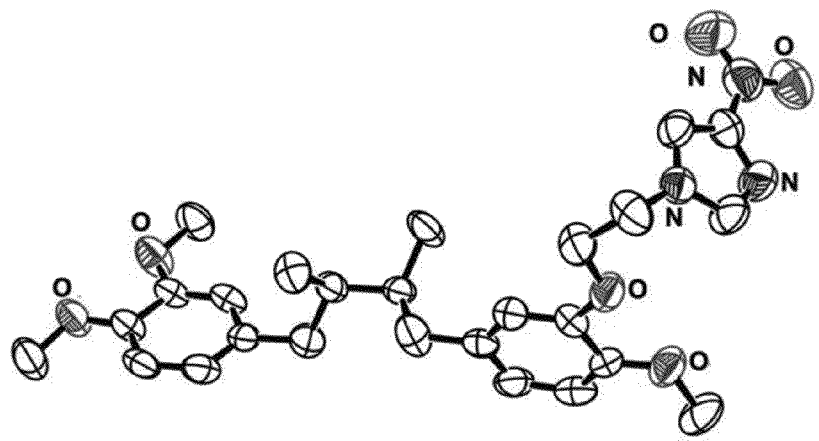
FIG. 4 is an ORTEP diagram of molecular framework 7a obtained by X-ray diffraction analysis.

Conjugate 7a may be generated in different regioisomeric forms. The first concern came from incorporation of the 4-nitroimidazole 6a onto NDGA bromide 5a: both of the N-1 and the N-3 nitrogen atoms of 6a may become the reacting centers. The second possibility came from the starting material 3, of which configuration is assigned as the 3'-hydroxy (not 4'-hydroxy) isomer on the basis of NMR spectroscopy. To assure configuration of the needle shape conjugate 7a, single crystal X-ray diffraction analysis was performed. Its molecular framework of triclinic crystals as shown in FIG. 4 possessed the space group P$_1^-$ with a=6.5191(15), b=10.596(3), c=20.024(5) Å, α=87.903(17)°, β=83.699(15)°, and γ=87.062(16)°. These results indicate that the imidazolization took place at the N-1 nitrogen atom. Moreover, the previous configuration assignment of the regioisomers 3 and 8 by NMR techniques was re-confirmed.

Figure 5:
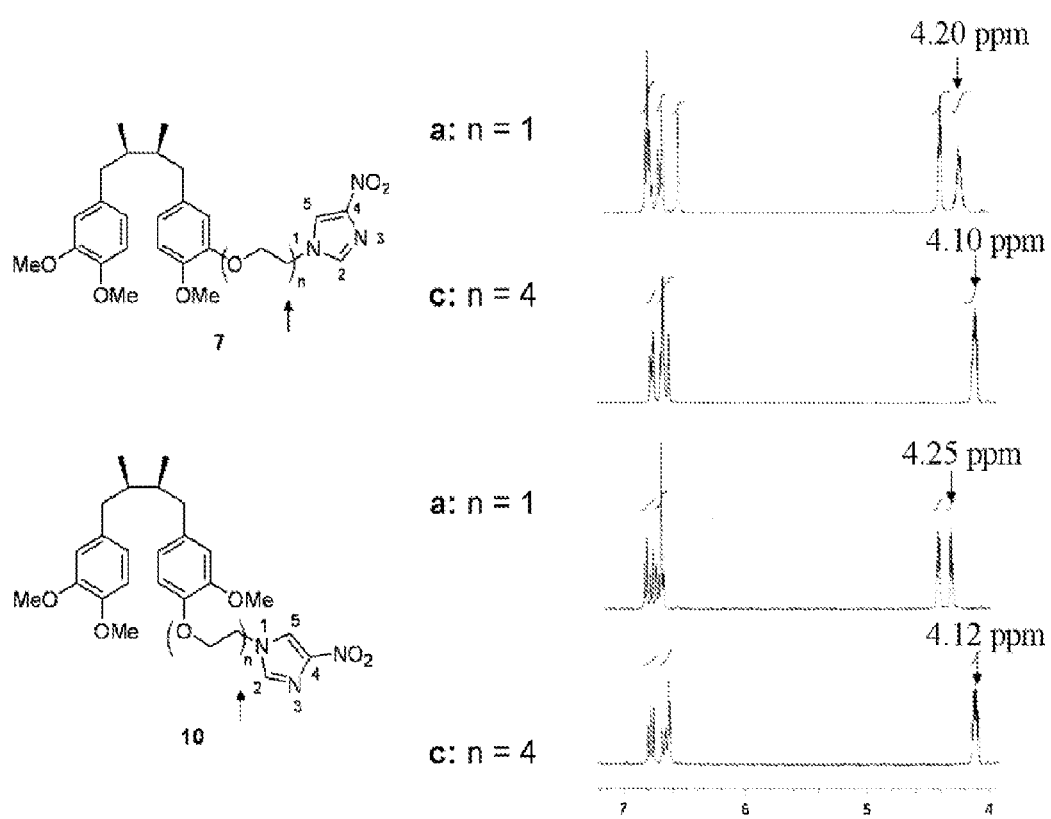
FIG. 5 is a partial 1H NMR spectra of compounds 7a, 7c, 10a, and 10c, with peaks between 4.10-4.25 ppm resulting from the α CH₂ protons attached to the N-1 nitrogen atom of the 4-imidazole moiety of the individual compounds.

Banerjee et al. (*Bioorg. Med. Chem. Lett.,* 2008, 18, 5233-7) reported that the α-CH$_2$ in the side chain attached directly to the N-1 nitrogen atom of the 4- and the 5-nitroimidazole derivatives show the proton resonance at 4.28 and 4.57 ppm, respectively. Conjugates 7a,c and 10a,c showed their resonances for the α-CH$_2$ protons between 4.10-4.25 ppm (FIG. 5). Therefore these conjugated compounds were assigned as the 4-nitroimidazol derivatives.

The aqueous solubility of all eight compounds was assessed by using a technique involving measurement of their UV absorbance[29]. The data listed in Table 1 indicate that the solubility was escalated 6.5-10.5 fold by the PEG tether in comparison with the —CH$_2$CH$_2$— tether (Table 1).

TABLE 1

Solubility of NDGA-nitroimidazole conjugates with and without a PEG tether

| Compound | Solubility (µg/mL) | Increment |
|---|---|---|
| 7a | 1.76 | 10.5 |
| 7c | 18.54 | |
| 7b | 1.64 | 8.1 |
| 7d | 13.21 | |
| 10a | 1.63 | 6.5 |
| 10c | 10.52 | |
| 10b | 1.70 | 11.2 |
| 10d | 19.12 | |

Example 2

Standard Procedure 1 for the Preparation of NDGA Bromides 5a,b, and 9a,b. To a solution containing a trimethyl NDGA (3 or 8) in ethanol or acetone was added potassium carbonate and an organic bromide (1,2-dibromoethane or 4). After the solution was heated at reflux overnight, the reaction mixture was cooled to room temperature. It was quenched with water (10.0 mL) and extracted with EtOAc (5×10.0 mL). The combined organic layers were washed with saturated aqueous NaCl (5.0 mL), dried over MgSO$_{4(s)}$, filtered, and concentrated under reduced pressure. The residue was purified by use of column chromatography to give the desired NDGA bromide. Purity of products 5a,b, and 9a,b was >98.5%, as checked by HPLC.

Example 3

Synthesis of (±)-(2R,3S)-1-[3-(2-Bromoethoxy)-4-methoxyphenyl]-4-(3,4-dimethoxyphenyl)-2,3-dimethylbutane (5a). The Standard Procedure 1 was followed by use of 3 (86.4 mg, 0.251 mmol, 1.0 equiv), potassium carbonate (69.4 mg, 0.502 mmol, 2.0 equiv), and 1,2-dibromoethane (944.0 mg, 5.025 mmol, 20 equiv) in ethanol (10.0 mL). After workup and purification with column chromatography (25% EtOAc in hexanes as eluant), 5a (61.7 mg, 0.137 mmol) was obtained in 55% yield as white solids: mp (recrystallized from dichoromethane) 79.0-79.5° C.; $^1$H NMR (CDCl$_3$, 400 MHz) δ 0.82 (d, J=6.8 Hz, 3H, CH$_3$), 0.83 (d, J=6.4 Hz, 3H, CH$_3$), 1.72-1.75 (m, 2H, 2×CH), 2.23-2.31 (m, 2H, 2×ArCH), 2.70-2.74 (m, 2H, 2×ArCH), 3.63 (t, J=7.0 Hz, 2H, CH$_2$Br), 3.82

(s, 3H, OCH$_3$), 3.83 (s, 3H, OCH$_3$), 3.84 (s, 3H, OCH$_3$), 4.28 (t, J=6.8 Hz, 2H, CH$_2$O), 6.63-6.68 (m, 3H, 3×ArH), 6.72-6.80 (m, 3H, 3×ArH); $^{13}$C NMR (CDCl$_3$, 100 MHz) δ 16.16, 16.19, 29.06, 38.57, 38.84, 39.14, 39.20, 55.77, 55.87, 56.07, 69.26, 110.95, 112.02, 112.16, 115.92, 120.87, 122.56, 134.36, 134.64, 147.00, 147.10, 147.87, 148.64; IR (neat) 2956 (s), 2931 (s), 1608 (w), 1590 (w), 1516 (s), 1464 (m), 1456 (m), 1261 (s), 1236 (s), 1029 (s) cm$^{-1}$; HRMS (FAB) m/z calcd for C$_{23}$H$_{31}$BrO$_4$: 450.1406, 452.1385. found: 450.1405, 452.1386.

Example 4

Synthesis of (±)-(2R,3S)-1-[3-(12-Bromo-1,4,7,10-tetraoxadodecanyl)-4-methoxyphenyl]-4-(3,4-dimethoxyphenyl)-2,3-dimethylbutane (5b). The Standard Procedure 1 was followed by use of 3 (101.2 mg, 0.2942 mmol, 1.0 equiv), potassium carbonate (85.3 mg, 0.617 mmol, 2.1 equiv), and 4 (1.883 g, 5.885 mmol, 20 equiv) in acetone (25.0 mL). After workup and purification with column chromatography (50% EtOAc in hexanes as eluant), 5b (135.1 mg, 0.2315 mmol) was obtained in 79% yield as a yellow gummy oil: $^1$H NMR (CDCl$_3$, 400 MHz) δ 0.81 (d, J=6.4 Hz, 6H, 2×CH$_3$), 1.72-1.74 (m, 2H, 2×CH), 2.23-2.29 (m, 2H, 2×ArCH), 2.69-2.75 (m, 2H, 2×ArCH), 3.44 (t, J=6.4 Hz, 2H, CH$_2$Br), 3.65-3.87 (m, 21H, 3×OCH$_3$+6×OCH$_2$), 4.14 (t, J=5.2 Hz, 2H, CH$_2$O), 6.62 (s, 1H, ArH), 6.66-6.68 (m, 2H, 2×ArH), 6.76-6.78 (m, 3H, 3×ArH); $^{13}$C NMR (CDCl$_3$, 100 MHz) δ 16.12, 16.17, 30.28, 38.77, 39.20, 39.25, 55.75, 55.84, 55.98, 68.42, 69.65, 70.47, 70.56, 70.62, 70.76, 71.14, 110.95, 111.67, 112.16, 114.80, 120.89, 121.60, 134.42, 134.45, 146.97, 147.59, 147.95, 148.63; IR (neat) 2955 (s), 2928 (s), 1607 (w), 1589 (w), 1516 (s), 1464 (m), 1421 (w), 1261 (s), 1237 (s), 1030 (s) cm$^{-1}$; HRMS (FAB) m/z calcd for C$_{29}$H$_{43}$BrO$_7$: 582.2192, 584.2172. found: 582.2194, 584.2167.

Example 5

Synthesis of (±)-(2R,3S)-1-[4-(2-Bromoethoxy)-3-methoxyphenyl]-4-(3,4-dimethoxyphenyl)-2,3-dimethylbutane (9a). The Standard Procedure 1 was followed by use of 8 (54.3 mg, 0.158 mmol, 1.0 equiv), potassium carbonate (45.6 mg, 0.330 mmol, 2.1 equiv), and 1,2-dibromoethane (663.5 mg, 3.532 mmol, 22 equiv) in ethanol (10.0 mL). After workup and purification with column chromatography (25% EtOAc in hexanes as eluant), 9a (36.2 mg, 0.0805 mmol) was obtained in 51% yield as white solids: mp (recrystallized from dichoromethane) 76.4-76.9° C.; $^1$H NMR (CDCl$_3$, 400 MHz) δ 0.82 (d, J=6.4 Hz, 3H, CH$_3$), 0.83 (d, J=6.4 Hz, 3H, CH$_3$), 1.74-1.75 (m, 2H, 2×CH), 2.24-2.32 (m, 2H, 2×ArCH), 2.70-2.76 (m, 2H, 2×ArCH), 3.62 (t, J=6.8 Hz, 2H, CH$_2$Br), 3.82 (s, 3H, OCH$_3$), 3.83 (s, 3H, OCH$_3$), 3.84 (s, 3H, OCH$_3$), 4.28 (t, J=6.8 Hz, 2H, CH$_2$O), 6.64-6.68 (m, 4H, 4×ArH), 6.76-6.82 (m, 2H, 2×ArH); $^{13}$C NMR (CDCl$_3$, 100 MHz) δ 16.14, 16.21, 29.04, 38.79, 38.85, 39.11, 39.20, 55.77, 55.85, 55.92, 69.40, 110.92, 112.16, 113.06, 114.82, 120.87, 121.09, 134.35, 136.21, 145.35, 146.99, 148.64, 149.59; IR (neat) 2956 (s), 2929 (s), 1607 (m), 1590 (m), 1516 (s), 1464 (m), 1456 (m), 1261 (s), 1235 (s), 1030 (s) cm$^{-1}$; HRMS (FAB) m/z calcd for C$_{23}$H$_{31}$BrO$_4$: 450.1406, 452.1385. found: 450.1409, 452.1386.

Example 6

Synthesis of (±)-(2R,3S)-1-[4-(12-Bromo-1,4,7,10-tetraoxadodecanyl)-3-methoxyphenyl]-4-(3,4-dimethoxyphenyl)-2,3-dimethylbutane (9b). The Standard Procedure 1 was followed by use of 8 (130.0 mg, 0.3779 mmol, 1.0 equiv), potassium carbonate (117.3 mg, 0.8487 mmol, 2.2 equiv), and 4 (2.4143 g, 7.5447 mmol, 20 equiv) in acetone (25.0 mL). After workup and purification with column chromatography (50% EtOAc in hexanes as eluant), 9b (190.6 mg, 0.3273 mmol) was obtained in 87% yield as a yellow gummy oil: $^1$H NMR (CDCl$_3$, 400 MHz) δ 0.82 (d, J=6.4 Hz, 3H, CH$_3$), 0.83 (d, J=6.4 Hz, 3H, CH$_3$), 1.57-1.74 (m, 2H, 2×CH), 2.25-2.30 (m, 2H, 2×ArCH), 2.71-2.75 (m, 2H, 2×ArCH), 3.44 (t, J=6.2 Hz, 2H, CH$_2$Br), 3.65-3.87 (m, 21H, 3×OCH$_3$+6×OCH$_2$), 4.14 (t, J=5.2 Hz, 2H, CH$_2$O), 6.63-6.68 (m, 4H, 4×ArH), 6.76-6.81 (m, 2H, 2×ArH); $^{13}$C NMR (CDCl$_3$, 100 MHz) δ 16.13, 16.17, 30.30, 38.74, 38.80, 39.10, 39.17, 55.73, 55.78, 55.82, 68.49, 69.65, 70.45, 70.54, 70.61, 70.71, 71.12, 110.87, 112.12, 112.69, 113.58, 120.84, 120.95, 134.37, 135.13, 146.16, 146.93, 148.58, 149.22; IR (neat) 2925 (s), 2868 (s), 1589 (w), 1515 (s), 1454 (m), 1418 (s), 1260 (s), 1235 (s), 1140 (s), 1029 (m) cm$^{-1}$; HRMS (FAB) m/z calcd for C$_{29}$H$_{43}$BrO$_7$: 582.2192, 584.2172. found: 582.2191, 584.2166.

Example 7

Standard Procedure 2 for the Preparation of Compounds 7a-d, and 10a-d. To a solution containing an organic bromide (5a,b or 9a,b) in DMF (3.0 mL) was added a base (sodium methoxide or potassium carbonate) and a nitroimidazole (6a or 6b). After the solution was stirred at 80° C. overnight, the reaction mixture was cooled to room temperature. It was quenched with water (5.0 mL), neutralize with 1.0 N HCl$_{(aq)}$ until pH=8.0, and then extracted with EtOAc (5×5.0 mL). The combined organic layers were washed with saturated aqueous NaCl (5.0 mL), dried over Na$_2$SO$_{4(s)}$, filtered, and concentrated under reduced pressure. The residues were purified by use of column chromatography to give the desired products. Purity of products 7a-d, and 10a-d was >98.2%, as checked by HPLC.

Example 8

(±)-(2R,3S)-4-(3,4-Dimethoxyphenyl)-1-[4-methoxy-3-[2-(4-nitro-1H-imidazol-1-yl)ethoxy]phenyl]-2,3-dimethylbutane (7a). The Standard Procedure 2 was followed by use of 5a (58.2 mg, 0.129 mmol, 1.0 equiv), sodium methoxide (15.4 mg, 0.285 mmol, 2.2 equiv), and 4-nitroimidazole (6a, 29.3 mg, 0.259 mmol, 2.0 equiv). After workup and purification with column chromatography (80% EtOAc in hexanes as eluant), 7a (38.1 mg, 0.0789 mmol) was obtained in 61% yield as white solids: mp (recrystallized from methanol) 80.4-81.0° C.; $^1$H NMR (CDCl$_3$, 400 MHz) δ 0.79 (d, J=6.8 Hz, 3H, CH$_3$), 0.83 (d, J=6.4 Hz, 3H, CH$_3$), 1.59-1.76 (m, 2H, 2×CH), 2.17-2.35 (m, 2H, 2×ArCH), 2.67-2.71 (m, 2H, 2×ArCH), 3.82 (s, 3H, OCH$_3$), 3.83 (s, 3H, OCH$_3$), 3.84 (s, 3H, OCH$_3$), 4.18-4.22 (m, 2H, CH$_2$N), 4.36 (t, J=4.6 Hz, 2H, CH$_2$O), 6.51 (s, 1H, ArH), 6.65-6.68 (m, 2H, 2×ArH), 6.73-6.78 (m, 3H, 3×ArH), 7.60 (s, 1H, nitroimidazole C5-H), 8.12 (s, 1H, nitroimidazole C2-H); $^{13}$C NMR (CDCl$_3$, 100 MHz) δ 16.06, 16.20, 38.25, 38.95, 39.04, 39.06, 47.92, 55.77, 55.81, 55.92, 68.08, 111.17, 111.66, 112.45, 115.50, 120.60, 120.90, 123.10, 134.34, 134.58, 136.56, 146.66, 146.99, 147.82, 148.03, 148.60; IR (neat) 2957 (s), 2933 (s), 1589 (w), 1543 (s), 1516 (s), 1455 (w), 1337 (s), 1261 (s), 1236 (s), 1029 (s) cm$^{-1}$; HRMS (FAB) m/z calcd for C$_{26}$H$_{34}$N$_3$O$_6$ (M+H)$^+$: 484.2448. found: 484.2444.

Example 9

(±)-(2R,3S)-4-(3,4-Dimethoxyphenyl)-1-[4-methoxy-3-[2-(2-nitro-1H-imidazol-1-yl)ethoxy]phenyl]-2,3-dimethylbutane (7b). The Standard Procedure 2 was followed by use of 5a (57.9 mg, 0.129 mmol, 1.0 equiv), sodium methoxide (15.4 mg, 0.285 mmol, 2.2 equiv), and 2-nitroimidazole (6b, 29.3 mg, 0.259 mmol, 2.0 equiv). After workup and purification with column chromatography (80% EtOAc in hexanes as eluant), 7b (32.9 mg, 0.0682 mmol) was obtained in 53% yield as a yellow gummy oil: $^1$H NMR (CDCl$_3$, 400 MHz) δ 0.79 (d, J=6.8 Hz, 3H, CH$_3$), 0.82 (d, J=6.8 Hz, 3H, CH$_3$), 1.70-1.72 (m, 2H, 2×CH), 2.21-2.31 (m, 2H, 2×ArCH), 2.67-2.73 (m, 2H, 2×ArCH), 3.75 (s, 3H, OCH$_3$), 3.83 (s, 3H, OCH$_3$), 3.85 (s, 3H, OCH$_3$), 4.30 (t, J=3.8 Hz, 2H, CH$_2$N), 4.81 (t, J=4.6 Hz, 2H, CH$_2$O), 6.56 (m, 1H, ArH), 6.63-6.68 (m, 2H, 2×ArH), 6.71-6.78 (m, 2H, 3×ArH), 7.13 (s, 1H, nitroimidazole C5-H), 7.35 (s, 1H, nitroimidazole C4-H); $^{13}$C NMR (CDCl$_3$, 100 MHz) δ 15.95, 15.99, 38.27, 38.68, 38.94, 39.02, 49.41, 55.59, 55.62, 55.69, 67.78, 110.86, 111.68, 112.12, 115.69, 120.73, 122.78, 127.46, 127.87, 134.18, 134.46, 144.51, 146.72, 146.82, 147.68, 148.43; IR (neat) 2924 (s), 2851 (s), 1588 (w), 1537 (w), 1515 (s), 1488 (w), 1361 (s), 1260 (s), 1235 (s), 1028 (s) cm$^{-1}$; HRMS (FAB) m/z calcd for C$_{26}$H$_{34}$N$_3$O$_6$ (M+H)$^+$: 484.2448. found: 484.2433.

Example 10

(±)-(2R,3S)-4-(3,4-Dimethoxyphenyl)-1-[4-methoxy-3-[12-(4-nitro-1H-imidazol-1-yl)-1,4,7,10-tetraoxadodecanyl]phenyl]-2,3-dimethylbutane (7c). The Standard Procedure 2 was followed by use of 5b (130.8 mg, 0.2241 mmol, 1.0 equiv), potassium carbonate (63.6 mg, 0.460 mmol, 2.1 equiv), and 4-nitroimidazole (6a, 50.2 mg, 0.444 mmol, 2.0 equiv). After workup and purification with column chromatography (100% EtOAc as eluant), 7c (121.3 mg, 0.1971 mmol) was obtained in 88% yield as a yellow gummy oil: $^1$H NMR (CDCl$_3$, 400 MHz) δ 0.80 (d, J=6.0 Hz, 6H, 2×CH$_3$), 1.71-1.72 (m, 2H, 2×CH), 2.22-2.28 (m, 2H, 2×ArCH), 2.69-2.73 (m, 2H, 2×ArCH), 3.61-3.85 (m, 21H, 3×OCH$_3$+6×OCH$_2$), 4.08-4.12 (m, 4H, CH$_2$N+CH$_2$O), 6.61 (s, 1H, ArH), 6.65-6.68 (m, 3H, 3×ArH), 6.74-6.77 (m, 2H, 2×ArH), 7.46 (d, J=1.0 Hz, 1H, nitroimidazole C5-H), 7.87 (d, J=1.0 Hz, 1H, nitroimidazole C2-H); $^{13}$C NMR (CDCl$_3$, 100 MHz) δ 15.97, 16.00, 38.54, 38.59, 39.01, 39.04, 48.02, 55.59, 55.69, 55.77, 68.26, 69.30, 69.49, 70.32, 70.37, 70.40, 70.49, 110.87, 111.58, 112.07, 114.57, 120.17, 120.77, 121.47, 134.30, 134.40, 136.45, 146.80, 147.33, 147.69, 147.76, 148.48; IR (neat) 2924 (s), 2868 (s), 1607 (w), 1589 (w), 1516 (s), 1456 (m), 1335 (s), 1260 (s), 1236 (s), 1028 (s) cm$^{-1}$; HRMS (FAB) m/z calcd for C$_{32}$H$_{46}$N$_3$O$_9$ (M+H)$^+$: 616.3234. found: 616.3239.

Example 11

(±)-(2R,3S)-4-(3,4-Dimethoxyphenyl)-1-[4-methoxy-3-[12-(2-nitro-1H-imidazol-1-yl)-1,4,7,10-tetraoxadodecanyl]phenyl]-2,3-dimethylbutane (7d). The Standard Procedure 2 was followed by use of 5b (135.1 mg, 0.2315 mmol, 1.0 equiv), potassium carbonate (67.5 mg, 0.488 mmol, 2.1 equiv), and 2-nitroimidazole (6b, 54.3 mg, 0.485 mmol, 2.0 equiv). After workup and purification with column chromatography (80% EtOAc in hexanes as eluant), 7d (121.2 mg, 0.1970 mmol) was obtained in 85% yield as a yellow gummy oil: $^1$H NMR (CDCl$_3$, 400 MHz) δ 0.81 (d, J=6.4 Hz, 6H, 2×CH$_3$), 1.73 (m, 2H, 2×CH), 2.23-2.29 (m, 2H, 2×ArCH), 2.69-2.74 (m, 2H, 2×ArCH), 3.56-3.86 (m, 21H, 3×OCH$_3$+6×OCH$_2$), 4.12 (t, J=5.0 Hz, 2H, CH$_2$N), 4.56 (t, J=4.8 Hz, 2H, CH$_2$O), 6.62 (s, 1H, ArH), 6.67-6.69 (m, 3H, 3×ArH), 6.75-6.78 (m, 2H, 2×ArH), 7.08 (s, 1H, nitroimidazole C5-H), 7.23 (s, 1H, nitroimidazole C4-H); $^{13}$C NMR (CDCl$_3$, 100 MHz) δ 16.05, 16.07, 38.63, 38.68, 39.09, 39.12, 49.71, 55.66, 55.76, 55.82, 68.30, 69.22, 69.58, 70.37, 70.46, 70.47, 70.61, 110.89, 111.56, 112.10, 114.58, 120.82, 121.56, 127.30, 127.86, 134.34, 134.40, 144.57, 146.88, 147.41, 147.77, 148.54; IR (neat) 2925 (s), 2873 (s), 1590 (w), 1538 (m), 1516 (s), 1456 (w), 1361 (s), 1260 (s), 1236 (s), 1029 (s) cm$^{-1}$; HRMS (FAB) m/z calcd for C$_{32}$H$_{46}$N$_3$O$_9$ (M+H)$^+$: 616.3234. found: 616.3231.

Example 12

(±)-(2R,3S)-4-(3,4-Dimethoxyphenyl)-1-[3-methoxy-4-[2-(4-nitro-1H-imidazol-1-yl)ethoxy]phenyl]-2,3-dimethylbutane (10a). The Standard Procedure 2 was followed by use of 9a (72.2 mg, 0.160 mmol, 1.0 equiv), sodium methoxide (19.1 mg, 0.353 mmol, 2.2 equiv), and 4-nitroimidazole (6a, 36.3 mg, 0.321 mmol, 2.0 equiv). After workup and purification with column chromatography (80% EtOAc in hexanes as eluant), 10a (50.3 mg, 0.104 mmol) was obtained in 65% yield as white solids: mp (recrystallized from methanol) 98.3-98.8° C.; $^1$H NMR (CDCl$_3$, 400 MHz) δ 0.80 (d, J=6.8 Hz, 3H, CH$_3$), 0.83 (d, J=6.8 Hz, 3H, CH$_3$), 1.74 (m, 2H, 2×CH), 2.22-2.34 (m, 2H, 2×ArCH), 2.69-2.76 (m, 2H, 2×ArCH), 3.81 (s, 3H, OCH$_3$), 3.83 (s, 3H, OCH$_3$), 3.84 (s, 3H, OCH$_3$), 4.25 (t, J=4.8 Hz, 2H, CH$_2$N), 4.37 (t, J=4.8 Hz, 2H, CH$_2$O), 6.62-6.68 (m, 4H, 4×ArH), 6.71-6.78 (m, 2H, 2×ArH), 7.60 (d, J=1.4 Hz, 1H, nitroimidazole C5-H), 8.13 (d, J=1.4 Hz, 1H, nitroimidazole C2-H); $^{13}$C NMR (CDCl$_3$, 100 MHz) δ 16.03, 16.16, 38.70, 38.93, 39.06, 39.25, 47.92, 55.61, 55.73, 55.82, 68.38, 110.98, 112.23, 112.78, 114.90, 120.62, 120.85, 120.93, 134.26, 136.55, 137.02, 144.90, 146.99, 147.98, 148.61, 149.66; IR (neat) 2957 (s), 2933 (s), 1590 (w), 1543 (s), 1516 (m), 1456 (w), 1337 (s), 1262 (m), 1235 (s), 1031 (s) cm$^{-1}$; HRMS (FAB) m/z calcd for C$_{26}$H$_{34}$N$_3$O$_6$ (M+H)$^+$: 484.2448. found: 484.2444.

Example 13

(±)-(2R,3S)-4-(3,4-Dimethoxyphenyl)-1-[3-methoxy-4-[2-(2-nitro-1H-imidazol-1-yl)ethoxy]phenyl]-2,3-dimethylbutane (10b). The Standard Procedure 2 was followed by use of 9a (38.2 mg, 0.0849 mmol, 1.0 equiv), sodium methoxide (10.1 mg, 0.187 mmol, 2.2 equiv), and 2-nitroimidazole (6b, 19.2 mg, 0.170 mmol, 2.0 equiv). After workup and purification with column chromatography (80% EtOAc in hexanes as eluant), 10b (21.6 mg, 0.0447 mmol) was obtained in 53% yield as a yellow gummy oil: $^1$H NMR (CDCl$_3$, 400 MHz) δ 0.79 (d, J=6.8 Hz, 3H, CH$_3$), 0.81 (d, J=6.8 Hz, 3H, CH$_3$), 1.72-1.73 (m, 2H, 2×CH), 2.23-2.32 (m, 2H, 2×ArCH), 2.68-2.74 (m, 2H, 2×ArCH), 3.73 (s, 3H, OCH$_3$), 3.82 (s, 3H, OCH$_3$), 3.83 (s, 3H, OCH$_3$), 4.30 (t, J=4.6 Hz, 2H, CH$_2$N), 4.80 (t, J=4.8 Hz, 2H, CH$_2$O), 6.59-6.70 (m, 5H, 5×ArH), 6.75-6.77 (m, 1H, ArH), 7.13 (s, 1H, nitroimidazole C5-H), 7.34 (s, 1H, nitroimidazole C4-H); $^{13}$C NMR (CDCl$_3$, 100 MHz) δ 16.04, 16.16, 38.69, 38.88, 39.05, 39.21, 49.64, 55.59, 55.72, 55.81, 68.30, 110.92, 112.16, 112.87, 115.24, 120.84, 121.02, 127.51, 128.03, 134.26, 136.84, 144.64, 145.10, 146.97, 148.60, 149.68; IR (neat) 2924 (s), 2853 (s), 1590 (w), 1539 (m), 1516 (s), 1456 (w), 1361 (s), 1261 (s), 1235 (s), 1030 (s) cm$^{-1}$; HRMS (FAB) m/z calcd for C$_{26}$H$_{34}$N$_3$O$_6$ (M+H)$^+$: 484.2448. found: 484.2457.

Example 14

(±)-(2R,3S)-4-(3,4-Dimethoxyphenyl)-1-[3-methoxy-4-[12-(4-nitro-1H-imidazol-1-yl)-1,4,7,10-tetraoxadodecanyl]phenyl]-2,3-dimethylbutane (10c). The Standard Procedure 2 was followed by use of 9b (146.6 mg, 0.2512 mmol, 1.0 equiv), potassium carbonate (74.4 mg, 0.538 mmol, 2.1 equiv), and 4-nitroimidazole (6a, 56.3 mg, 0.498 mmol, 2.0 equiv). After workup and purification with column chromatography (100% EtOAc as eluant), 10c (88.4 mg, 0.144 mmol) was obtained in 57% yield as a yellow gummy oil: $^1$H NMR (CDCl$_3$, 400 MHz) δ 0.81 (d, J=6.4 Hz, 3H, CH$_3$), 0.82 (d, J=6.4 Hz, 3H, CH$_3$), 1.73 (m, 2H, 2×CH), 2.23-2.31 (m, 2H, 2×ArCH), 2.70-2.75 (m, 2H, 2×ArCH), 3.62-3.86 (m, 21H, 3×OCH$_3$+6×OCH$_2$), 4.09-4.14 (m, 4H, CH$_2$N+CH$_2$O), 6.62-6.68 (m, 4H, 4×ArH), 6.76-6.80 (m, 2H, 2×ArH), 7.47 (s, 1H, nitroimidazole C5-H), 7.88 (s, 1H, nitroimidazole C2-H); $^{13}$C NMR (CDCl$_3$, 100 MHz) δ 16.12, 16.18, 38.74, 38.84, 39.12, 39.21, 48.24, 55.76, 55.78, 55.85, 68.60, 69.49, 69.69, 70.54 70.57, 70.65, 110.97, 112.21, 112.81, 113.66, 120.17, 120.89, 121.04, 134.41, 135.24, 136.48, 146.18, 146.98, 147.95, 148.63, 149.22; IR (neat) 2924 (s), 2854 (s), 1634 (w), 1589 (w), 1515 (s), 1456 (m), 1417 (m), 1334 (s), 1260 (s), 1028 (s) cm$^{-1}$; HRMS (FAB) m/z calcd for C$_{32}$H$_{46}$N$_3$O$_9$ (M+H)$^+$: 616.3234. found: 616.3232.

Example 15

(±)-(2R,3S)-4-(3,4-Dimethoxyphenyl)-1-[3-methoxy-4-[12-(2-nitro-1H-imidazol-1-yl)-1,4,7,10-tetraoxadodecanyl]phenyl]-2,3-dimethylbutane (10d). The Standard Procedure 2 was followed by use of 9b (36.6 mg, 0.0627 mmol, 1.0 equiv), potassium carbonate (18.0 mg, 0.130 mmol, 2.1 equiv), and 2-nitroimidazole (6b, 14.4 mg, 0.126 mmol, 2.0 equiv). After workup and purification with column chromatography (80% EtOAc in hexanes as eluant), 10d (32.1 mg, 0.0522 mmol) was obtained in 83% yield as a yellow gummy oil: $^1$H NMR (CDCl$_3$, 400 MHz) δ 0.81 (d, J=6.4 Hz, 3H, CH$_3$), 0.82 (d, J=6.4 Hz, 3H, CH$_3$), 1.73 (m, 2H, 2×CH), 2.25-2.31 (m, 2H, 2×ArCH), 2.73-2.75 (m, 2H, 2×ArCH), 3.57-3.86 (m, 21H, 3×OCH$_3$+6×OCH$_2$), 4.12 (t, J=5.0 Hz, 2H, CH$_2$N), 4.56 (t, J=4.8 Hz, 2H, CH$_2$O), 6.62-6.68 (m, 4H, 4×ArH), 6.75-6.79 (m, 2H, 2×ArH), 7.08 (s, 1H, nitroimidazole C5-H), 7.23 (s, 1H, nitroimidazole C4-H); $^{13}$C NMR (CDCl$_3$, 100 MHz) δ 16.08, 16.14, 38.71, 38.80, 39.06, 39.16, 49.77, 55.73, 55.76, 55.83, 68.56, 69.28, 69.67, 70.43 70.54, 70.65, 110.96, 112.20, 112.77, 113.64, 120.85, 120.95, 127.31, 127.91, 134.37, 135.23, 144.62, 146.12, 146.96, 148.61, 149.23; IR (neat) 2925 (s), 2868 (s), 1655 (w), 1590 (w), 1515 (s), 1488 (w), 1459 (m), 1362 (s), 1260 (s), 1030 (s) cm$^{-1}$; HRMS (FAB) m/z calcd for C$_{32}$H$_{46}$N$_3$O$_9$ (M+H)$^+$: 616.3234. found: 616.3234.

Example 16

Determination of Water Solubility of Compounds 7a-d and 10a-d. A saturated solution was prepared by addition of a test compound (7a-d and 10a-d; ca. 1.00 mg) to water (1.00 mL), which was sonicated at 25° C. for 5.0 min and stirring at room temperature for an additional 1.0 h. After filtration with Millipore filters (0.45-μm-pore-size polyvinylidene fluoride), the supernatant was analyzed by UV spectroscopy with concentration determined from absorbance, standardized against calibration data. Standard curves for each compound were obtained by plotting absorbance against concentration. The concentration range of the standard solutions was 1.0-10 μg/mL. For all standards, their curves were linear with γ>0.996.

Example 17

Antiproliferative activity. The anti-cancer activities of the parent compounds 3 and 8 and the conjugated compounds 7a-d and 10a-d were tested against Hep3B human hepatocellular carcinoma cells in culture. Our results, shown in Table 2, indicate that all of the newly designed conjugates exhibited appealing anti-cancer activity with IC$_{50}$ values between 10-25 μM. By scrutinizing these values, we deduce the following structure-activity relationships: (1) all of the conjugated compounds exhibited significantly more antiproliferative activity than either of the parent compounds; (2) there was no discernable difference in the potencies of 4-nitroimidazole and 2-nitroimidazole analogs; (3) the conjugated compounds with the nitroimidazole moiety attached at the 3'-position of NDGA were of similar potency to those attached at the 4'-position; and (4) the conjugate compounds with a PEG tether were more potent than those with a —CH$_2$CH$_2$— tether.

TABLE 2

Cytotoxic activity of trimethyl NDGA and trimethyl NDGA-nitroimidazole against Hep3B human hepatocellular carcinoma cells following a 72-h exposure under normoxic (21% O$_2$) and hypoxic (1.0% O$_2$) conditions (see Experimental section).

| Compound | IC$_{50}$$^a$ (μM)$^b$ Normoxic (N) |
|---|---|
| 3 | 45.2 ± 2.9 |
| 7a | 15.8 ± 1.6 |
| 7b | 21.8 ± 4.5 |
| 7c | 13.0 ± 5.1 |
| 7d | 12.6 ± 4.9 |
| 8 | 60.9 ± 1.5 |
| 10a | 18.7 ± 4.1 |
| 10b | 24.8 ± 8.7 |
| 10c | 12.5 ± 4.1 |
| 10d | 13.4 ± 3.4 |

$^a$IC$_{50}$ is the half maximal (50%) growth inhibitory concentration (IC) of the test compound.
$^b$IC$_{50}$ values were determined by non-linear regression analysis of data from at least three experiments performed in triplicate.

Example 18

Hypoxia targeting. Nitroimidazoles are converted to reactive compounds in hypoxic cells. Therefore it is of importance to compare the antiproliferative activities of the nitroimidazole conjugated compounds against Hep3B cells under normoxic and hypoxic conditions. In these experiments, Hep3B cells in culture were treated with each of the conjugated compounds 7c-d, 10c-d, or the parent compounds 3 or 8 for a 5.0-hour period under normoxic (21% O$_2$) or hypoxic (1.0% O$_2$) conditions. After treatment, the cells were returned to normal conditions and assayed for proliferation after 5 days of additional growth. Our results in Table 3 show that each of the conjugated compounds had greater antiproliferative activity under hypoxic conditions. Unexpectedly, the unconjugated parent compounds were also more active in hypoxic cells. The ratio between the IC$_{50}$ values for each drug under normoxic versus hypoxic culture conditions was computed and used as a measure of the relative increase in potency. While the derivatives of 3' hydroxylated trimethyl NDGA were no more effective under hypoxia than their parent compound (ratios of 1.62 and 1.14 compared with 1.58, Table 3), the derivatives of 4' trimethyl NDGA were noticeably more effective in hypoxic cells than their unconjugated counterpart (ratios of 2.6 and 2.42 compared with 1.28, Table 3).

TABLE 3

Effect of trimethyl NDGA and trimethyl NDGA-nitroimidazole conjugates on the proliferation of Hep3B human hepatocellular carcinoma cells following a 5-h exposure under normoxic (21% $O_2$) and hypoxic (1.0% $O_2$) conditions (see Experimental section).

| Compound | $IC_{50}^{a}$ (µM)[b] Normoxic (N) | $IC_{50}$ (µM) Hypoxic (H) | Ratio $IC_{50}$ (N)/$IC_{50}$ (H) |
|---|---|---|---|
| 3 | 156.1 ± 10.1 | 99.0 ± 0.6 | 1.58 |
| 7c | 104.1 ± 17.6 | 64.3 ± 15.1 | 1.62 |
| 7d | 60.8 ± 9.4 | 53.2 ± 8.0 | 1.14 |
| 8 | 112.2 ± 26.6 | 87.6 ± 8.7 | 1.28 |
| 10c | 140.0 ± 33.5 | 52.1 ± 3.8 | 2.69 |
| 10d | 118.6 ± 42.8 | 49.1 ± 4.9 | 2.42 |

[a]$IC_{50}$ is the half maximal (50%) growth inhibitory concentration (IC) of the test compound.
[b]$IC_{50}$ values were determined by non-linear regression analysis of data from three experiments (two experiments for compounds 3 and 8) performed in triplicate.

Example 19

Figure 6:
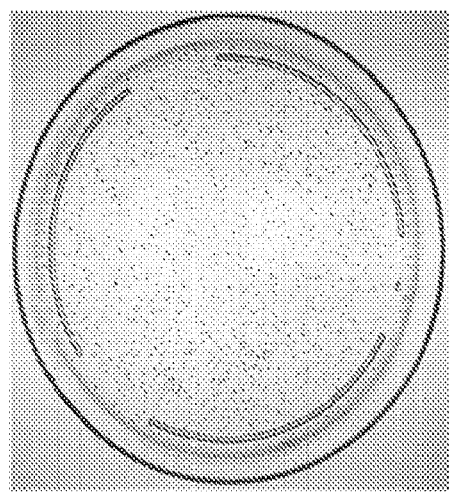
FIG. 6 depicts the plating efficiency of HT29 human colorectal carcinoma cells after treatment with DMSO, 40μ M3n and 40μ M3N-PEG-2NI. HT29 cells were treated for 48 h with 40 μM M3N, 40 μM M3N-PEG-2NI or the DMSO vehicle. At the end of the treatment period, the cells were diluted 10,000 fold and replated. Eight days later colonies were stained with methylene blue.
Figure 6:
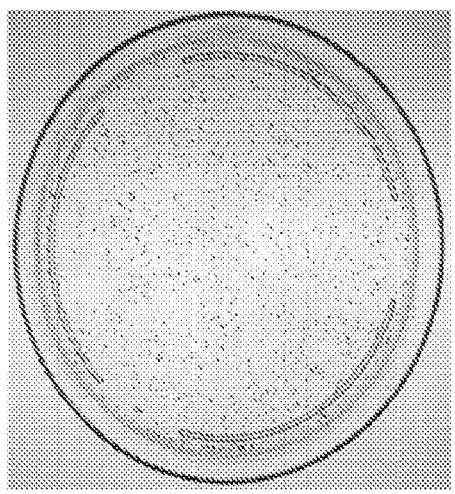
Figure 6:
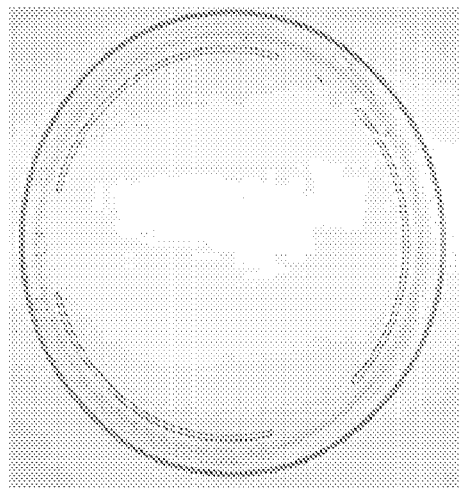

Effect of M3N-PEG-2NI on growth and viability of human cancer cells in culture. All drug treatments with M3N and M3N-PEG-2NI under normoxic conditions on HT29, 786-O, and Hep3B demonstrated that the latter was significantly more cytotoxic than the former. There was no significant difference between using M3N and M3N-PEG-2NI under normoxic and hypoxic conditions (Table 4). HT29 cells were used to test whether or not cells previously treated with M3N-PEG-2NI, M3N, and the control (DMSO) were able to replicate. HT29 cells treated with DMSO or 40 uM M3N were able to replicate after treatment. Cells treated with 40 uM M3N-PEG-2NI however, were unable to replicate (FIG. 6)

TABLE 4

$IC_{50}^{a}$ values for M3N and M3N-PEG-2NI against different tumor cell lines under normoxic conditions.

| Drug | HT29 ($IC_{50}$) | 786-0 ($IC_{50}$) | Hep3B ($IC_{50}$) |
|---|---|---|---|
| M3N | >80 µM | 36-64 µM | 15-30 µM |
| M3N-PEG-2NI | 4-6 µM | 10-14 µM | 4 µM |

[a]$IC_{50}$ is the half maximal (50%) growth inhibitory concentration (IC) of the test compound.

Example 20

Inhibition of primary tumor and abdominal tumor mass by M3N-TEG-2NI treatment. The efficacy of M3N-PEG-2NI against human colorectal cancer cells was further investigated using orthopically explanted HT29 tumors in nude mice. After three weeks of drug treatment, the average primary tumor weight of mice from the vehicle treated control group was 650+/−190 mg. In contrast, for mice treated with M3N-PEG-2N the average primary tumor weight was 300+/−140 mg indicating a dramatic reduction in the growth rate of the tumor in the cecum (Table 5).

All but one of the mice also developed tumor mass within regions of the abdominal cavity. Tumor mass surrounding the kidneys and ovaries or testes were collected and weighed and control group mice 1, 2, 3, and 4 had tumor mass surrounding the kidneys of <100 mg, 300 mg, 200 mg, and 300 mg, respectively. Mice 1 and 2 also had tumors surrounding the ovaries, with weights of <100 mg each. Mice 3 and 4 had tumors surrounding the testes, with weights of 400 mg each. From the treated group, mouse 5 developed tumor masses surrounding the kidneys and ovaries, with weights of <100 mg each. Mouse 6 of the treated group developed a tumor surrounding the ovaries, with a weight of <100 mg. The average weight of tumor mass in the abdominal cavity of the control group was 425+/−275 mg, while the average weight of tumor mass in the abdominal cavity of the treated group mice was 75+/−50 mg (Table 5). As such, M3N-PEG-2NI-treated mice had less tumor mass within their abdominal cavity after treatment.

The total tumor load was characterized as total tumor load as the weight of the primary tumor plus the weight of the total tumor mass. Thus, the average total tumor load of vehicle-treated mice was 1075+/−378 mg and the average total tumor load of M3N-PEG-2NI treated mice was 375+/−150 mg (Table 5). As such, the average total tumor load of M3N-PEG-2NI treated mice was dramatically less than that of the control mice.

TABLE 5

Effect of M3N-PEG-2NI treatment on tumor growth in an orthotopic xenograft mouse model of human colorectal cancer.

| Drug Treatment | Mean Primary Tumor and Mass (mg) | Mean Abdominal Cavity Tumor Mass (mg) | Mean Total Tumor Load (mg) | Body Weight Increase (%) |
|---|---|---|---|---|
| Vehicle | 650 ± 190 | 425 ± 275 | 1075 ± 378 | 13.2 |
| M3N-PEG-2NI | 300 ± 140 | 75 ± 50 | 375 ± 150 | 11.3 |

Example 21

Figure 8A:
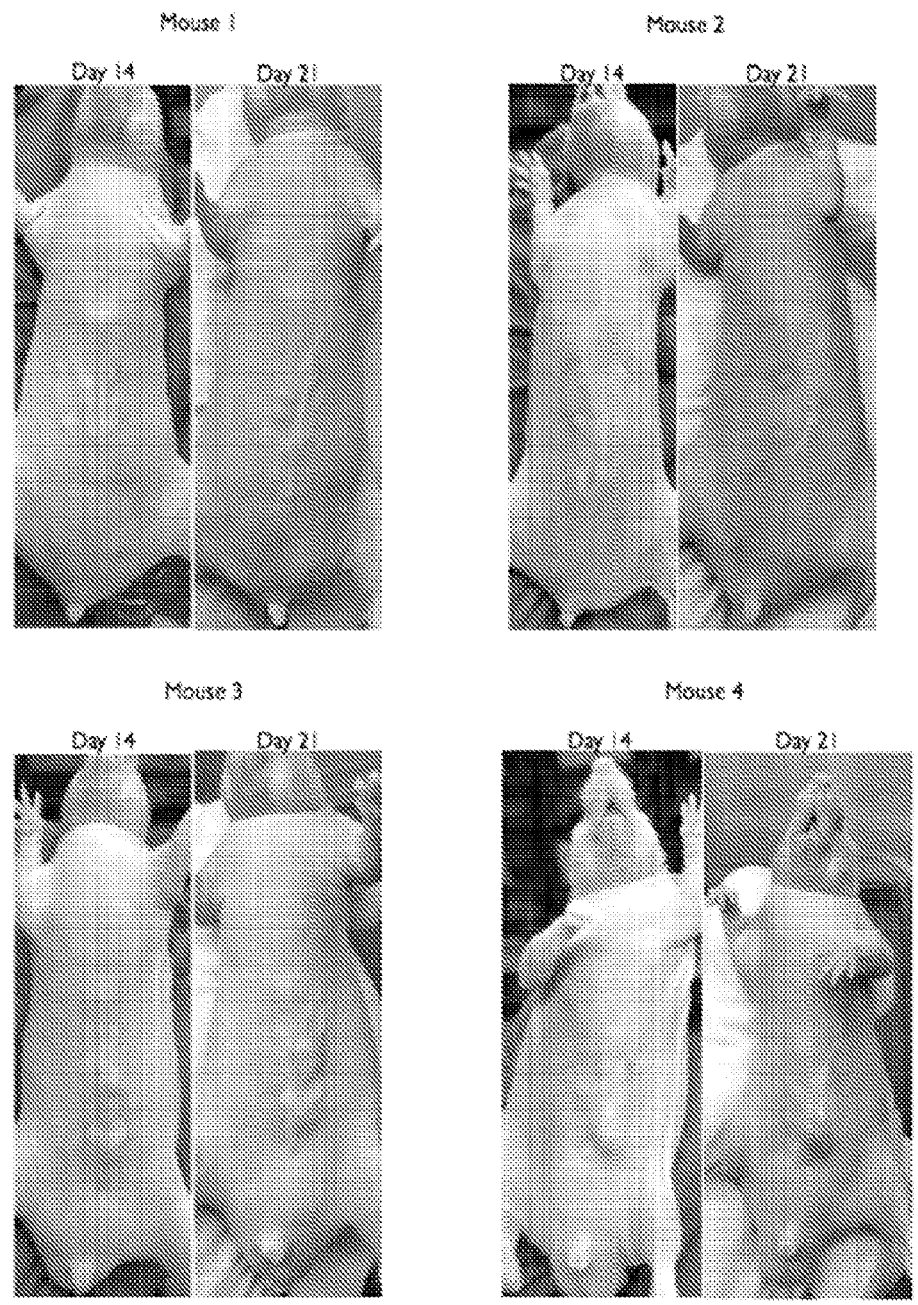
FIG. 8 presents the effect of 2NI-PEG-M3N on the presence of abdominal tumors in nude mice with orthotopic colorectal cancer explants. Photographs of the abdominal surface of control (8A) and treated (8B) mice showing the presence or absence of grossly visible tumor growth.
Figure 8B:
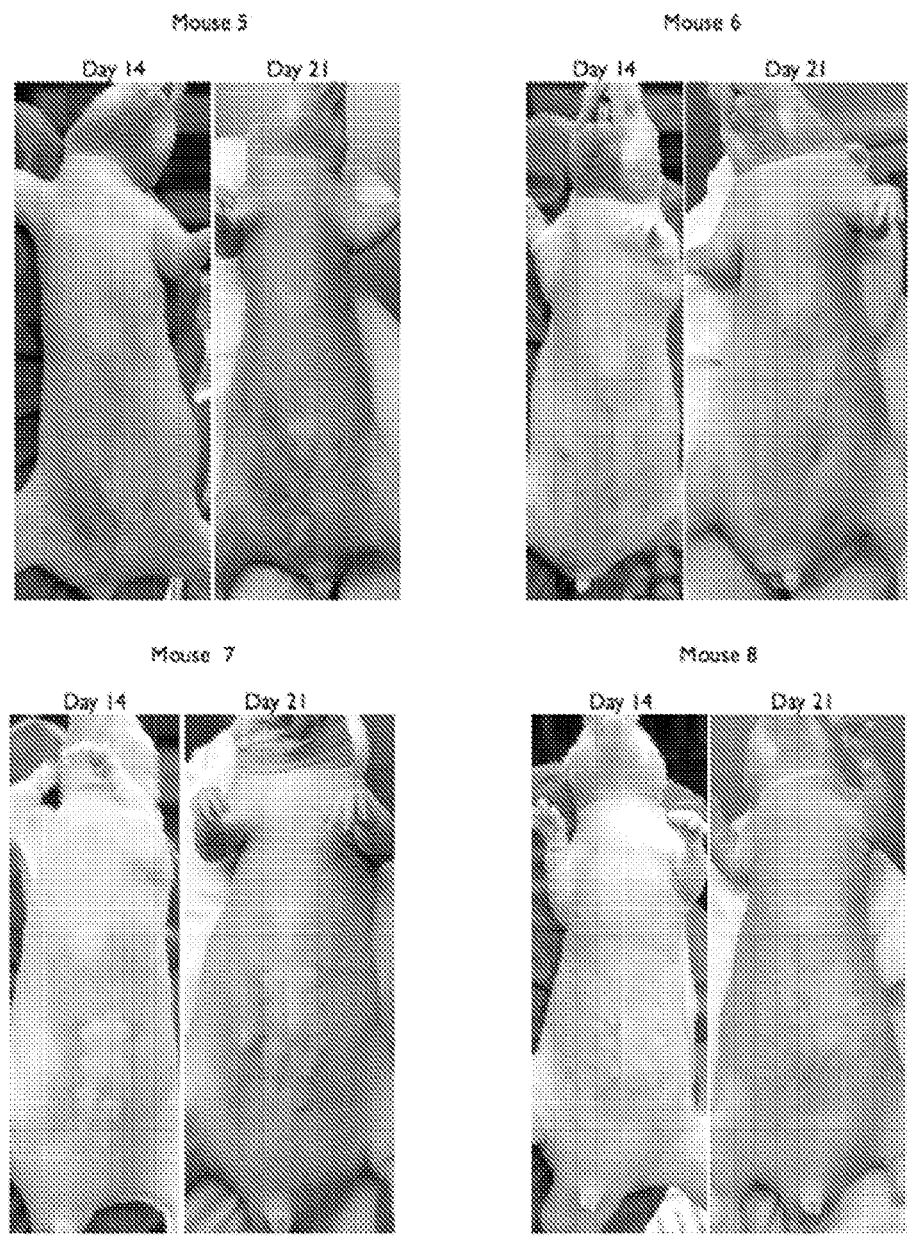
Figure 9:
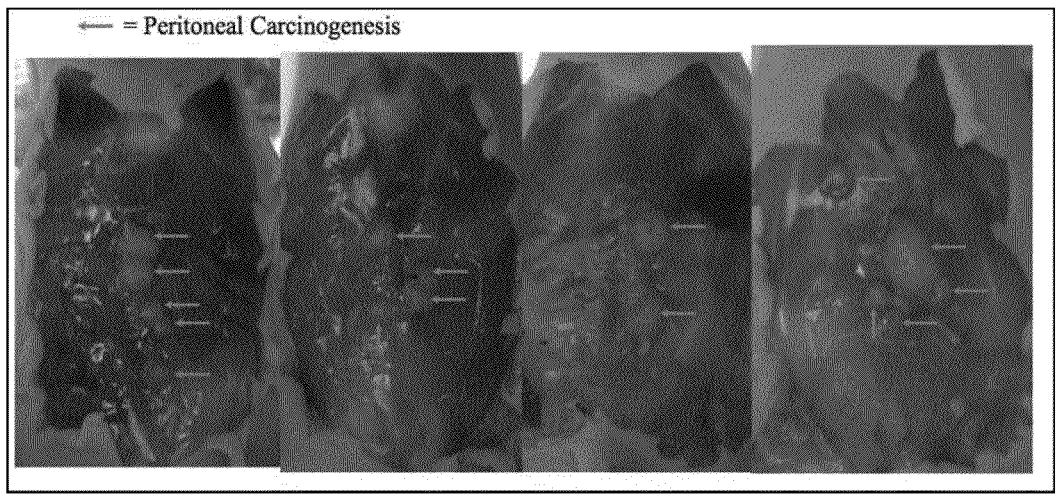
FIG. 9 depicts the effect of drug treatment on the formation of tumors in the peritoneal cavity. Euthanized control and treated mice were dissected to expose the peritoneal cavity. Blue arrows mark the locations of tumor growth within the peritoneum.
Figure 9:
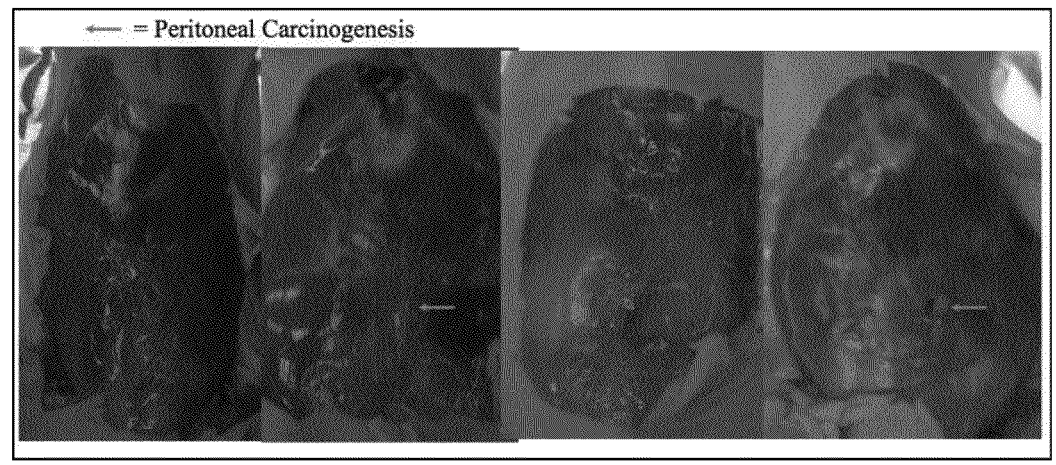

Inhibited peritoneal carcinogenesis by M3N-PEG-2NI treatment. Control mice 1, 2, 3, and 4 developed multiple, and in some cases, large peritoneal tumors by end of the treatment period (FIGS. 8 and 9) Mouse 1 (female) had 5, small peritoneal tumors, mouse 2 (female) had 4, small peritoneal tumors, mouse 3 had two large peritoneal tumors and mouse 4 had 1 large peritoneal tumor and 4 small peritoneal tumors. In the treated group mice 5 (female) and 7 (male) exhibited no peritoneal tumors, while mice 6 (female) and 8 (male) had a single, small peritoneal tumor. Mice treated with the vehicle developed significantly more peritoneal tumors than those treated with M3N-PEG-2NI.

Example 22

Figure 10:
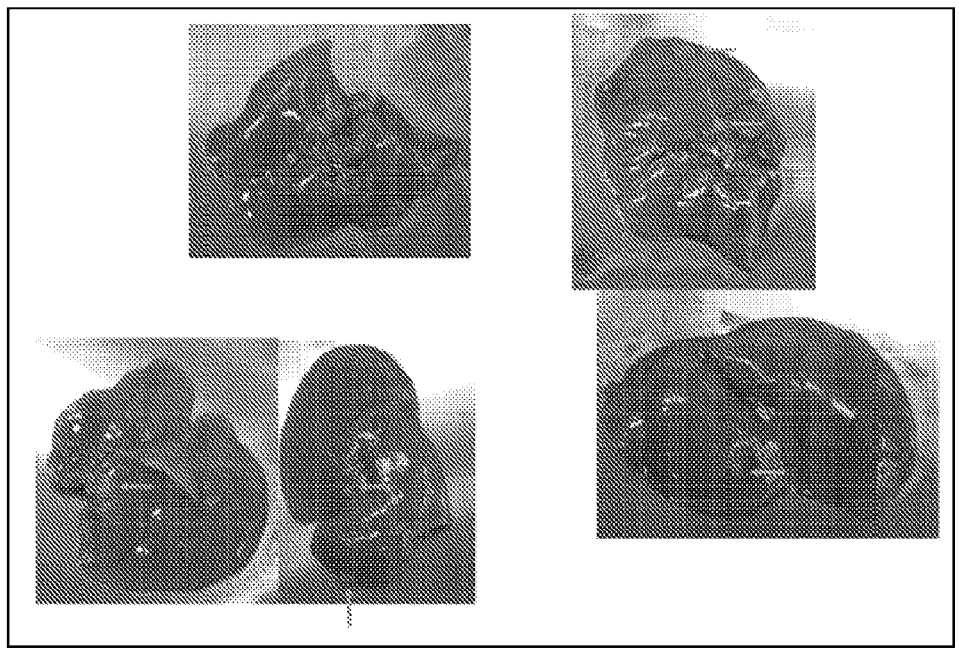
FIG. 10 shows gross analysis of metastasis in livers from control and M3N-PEG-2NI treated human colorectal cancer containing nude mice. Metastases are indicated by blue arrows.
Figure 10:
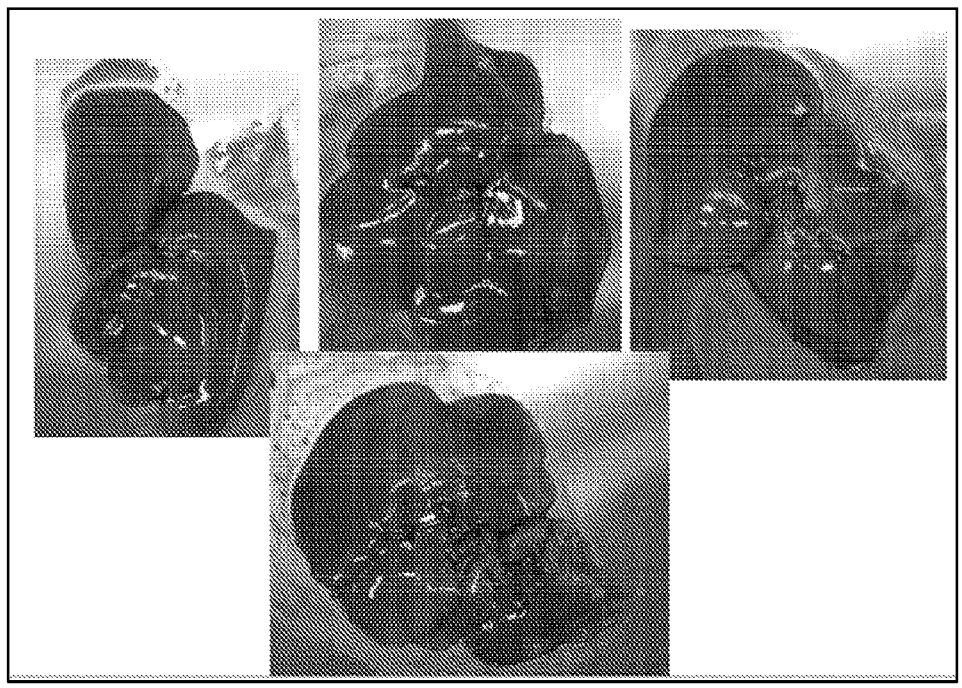

Suppression of liver metastasis by M3N-PEG-2NI treatment. Mice 1, 2, 3, and 4 (CPE-treated) all developed metastatic tumors (FIG. 10). Mice 1 and 4 developed single liver metastatic legions. Mouse 2 (female) developed 4 separate metastatic liver legions. Also, mouse 2's primary tumor adhered itself to the liver. Metastatic tumors were also seen along the diaphragm, along which the liver rested. Mouse 3 (male) developed 5 separated liver metastatic legions. Like mouse 2, mouse 3 also possessed 3 metastatic legions along its diaphragm, where the liver rested. Mice 5, 6, and 8 (all treated with M3N-PEG-2NI) had normal livers, with no metastatic legions present. Mouse 7, also M3N-PEG-2NI, developed a single metastatic legion on its liver. Thus, all 4 mice treated with placebo developed liver metastasis, while 1 of the 4 mice treated with M3N-PEG-2NI developed liver metastasis. These results, as such, demonstrate that M3N-PEG-2NI inhibited liver metastasis (FIG. 10). Whether or not the tumor mass within the abdominal cavity was the result of metastasis or simply localized spread of the primary tumor was not clear upon dissection. Histological analysis of the tumor mass cells will provide better insight into the nature of the tumor mass found within the abdominal cavity.

Example 23

Figure 11:
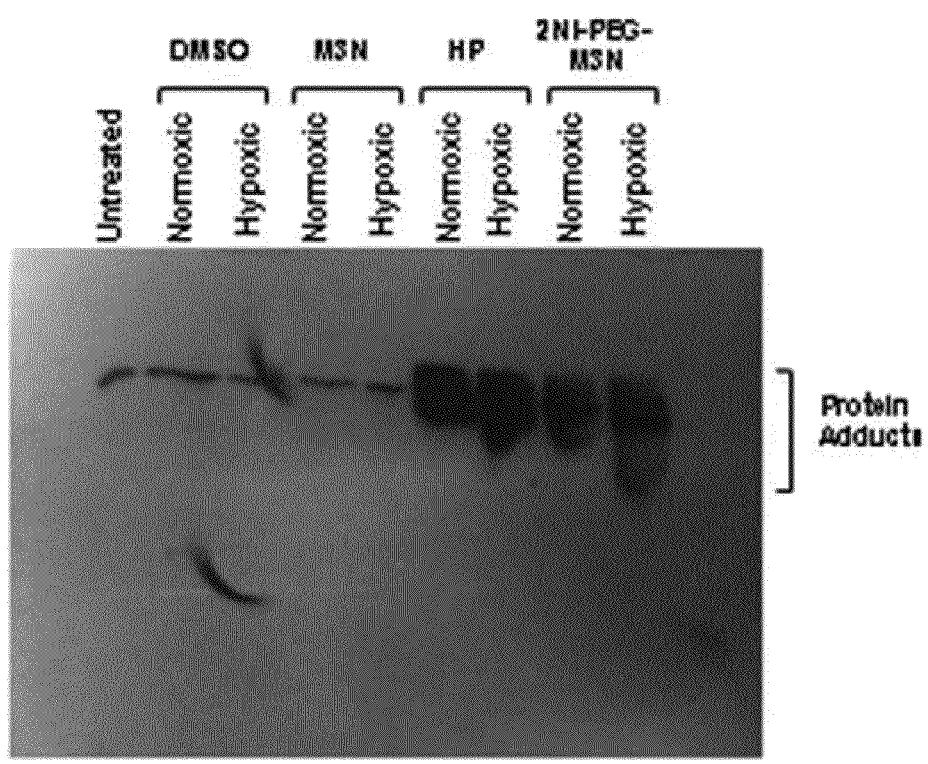
FIG. 11 presents a western blot analysis of proteins from LNCaP cells cultured in the presence of DMSO, M3N, Hydroxyprobe-1, or M3N-PEG-2NI under normoxic (20% O₂) or hypoxic (0.5% O₂) conditions. The presence of nitroimidazole-induced protein adducts were detected with the PAb2627 polyclonal antibody.
Figure 12:
FIG. 12 presents an immunofluorescence analysis of tissue sections from LNCaP tumor explants or adjacent tissue from nude mice treated for three weeks with Hydroxyprobe-1, M3N, or M3N-PEG-2NI. Protein adducts were visualized using the polyclonal antibody Pab2627.
Figure 12:
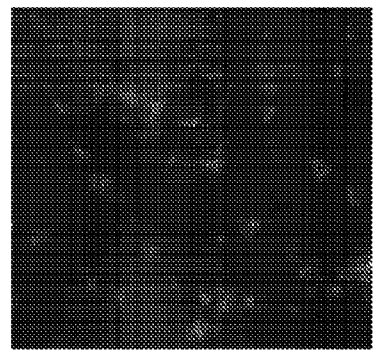
Figure 12:
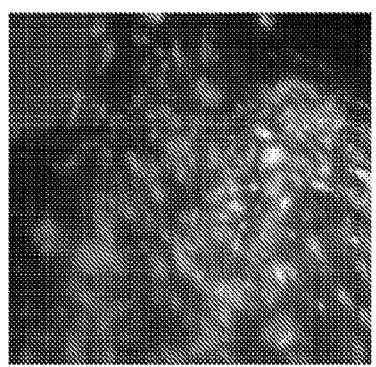
Figure 12:
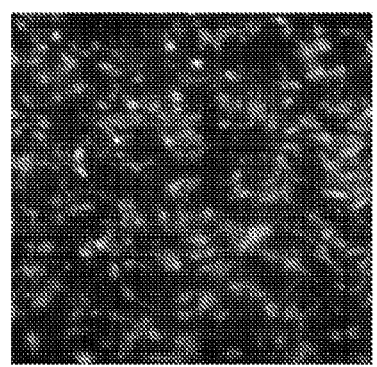
Figure 12:
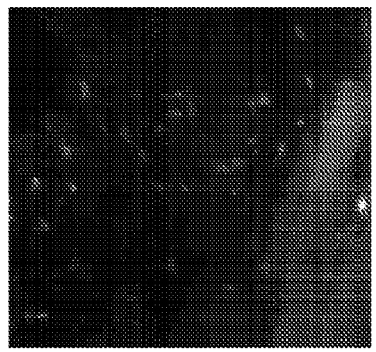
Figure 12:
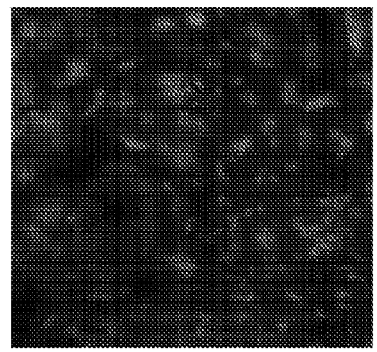
Figure 12:
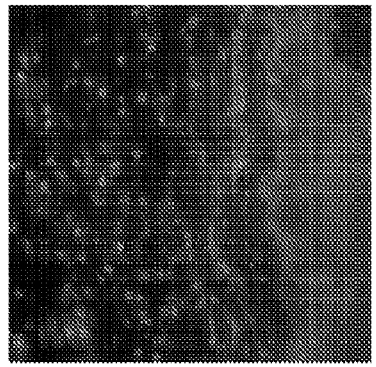
Figure 12:
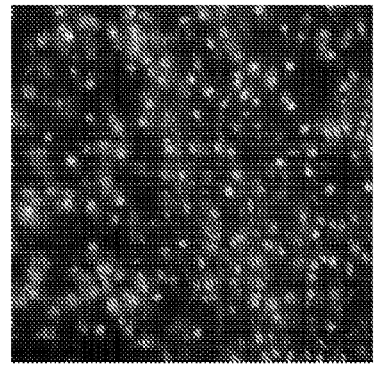

Formation of protein adducts by M3N-PEG-2NI in LNCaP prostate cancer cells in culture and in LNCaP tumor explants in nude mice. The hypoxia targeting mechanism of nitroimidazole-containing compounds is characterized by the formation of protein-adducts produced by the hypoxia activated nitroimidazole group. To determine if the M3N-PEG-2NI conjugate behaves in a similar manner, western blot analysis of treated cell lines and immunofluorescence analysis of tumor sections from treated mice were carried out with polyclonal antibody directed against Hydroxyprobe-1 induced protein adducts. Extracts of LNCaP human prostate cancer cells exposed in culture to M3N-PEG-2NI or Hydroxyprobe-1 showed evidence of protein adducts when examined by western blot analysis (FIG. 11). No protein adducts were detected in cells treated with M3N or the DMSO vehicle control. Protein-adducts were also found in LNCaP tumor explants of nude mice treated with M3N-PEG-2NI or the Hydroyprobe-1 (FIG. 12) Immunofluorescence staining was reduced in normal tissue adjacent to the tumor. There was little evidence of adduct formation in tumors from M3N-treated mice.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:
1. A compound of Formula I:

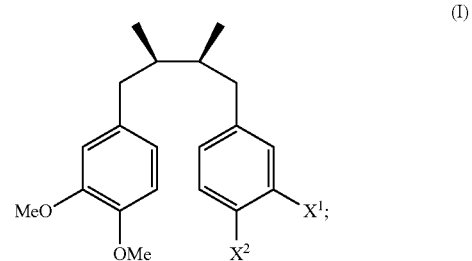

(I)

wherein $X^1$ and $X^2$ cannot be the same and are selected from the group consisting of H, OMe, and a imidazole moiety of Formula Ia:

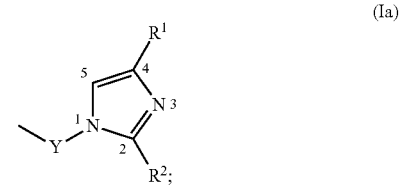

(Ia)

with the proviso that one of $X^1$ and $X^2$ must be the imidazole moiety of Formula Ia;
wherein $R^1$ and $R^2$ are the same or different, and are each selected from the group consisting of H and electron withdrawing groups; and
wherein Y is a linking group consisting of a water soluble polymer having n subunits, wherein n is an integer from 1 to 10, and wherein the polymer is selected from the group consisting of polyethylene glycol, polyvinyl alcohol, polycaprolactone, polypropylene glycol, polyethyloxazoline, and poly-L-lactic acid and related synthetic hydrophilic polymers thereof.

2. The compound, salt, solvate, or stereoisomer of claim 1, wherein the compound is a compound of Formula (IV):

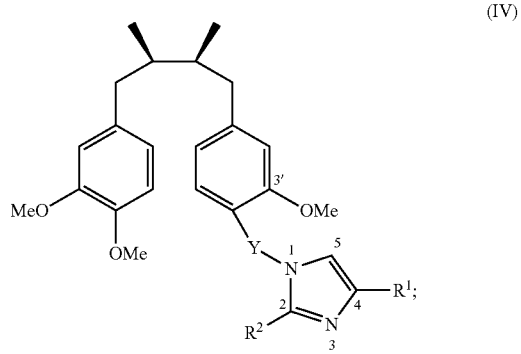

(IV)

wherein $R^1$ and $R^2$ are the same or different, and are each selected from the group consisting of H and electron withdrawing groups; and wherein Y is a linking group consisting of a water soluble polymer having n subunits, wherein n is an integer from 1 to 10, and wherein the polymer is selected from the group consisting of polyethylene glycol, polyvinyl alcohol, polycaprolactone, polypropylene glycol, polyethyloxazoline, and poly-L-lactic acid and synthetic hydrophilic polymers thereof.

3. The compound, salt, solvate, or stereoisomer of claim 2, wherein the electron withdrawing group is selected from the group consisting of $SCN$, $N_3$, $CN$, $SO_3H$, $B(OH)_2$, $PO(OH)_2$, $SO_2NHOH$, $SO_2NH_2$, $CONHOH$, $NO_2$, $CHO$, $COOR"$, $COR"$, $NR"_3+$, wherein $R"$ is H or $C_1$-$C_6$ alkyl, and $CZ_3$, wherein Z is F, Cl, or Br.

4. The compound, salt, solvate, or stereoisomer of claim 3, wherein n=1.

5. The compound, salt, solvate, or stereoisomer of claim 3, wherein n=4.

6. The compound, salt, solvate, or stereoisomer of claim 5, wherein the compound is a compound of Formula (V):

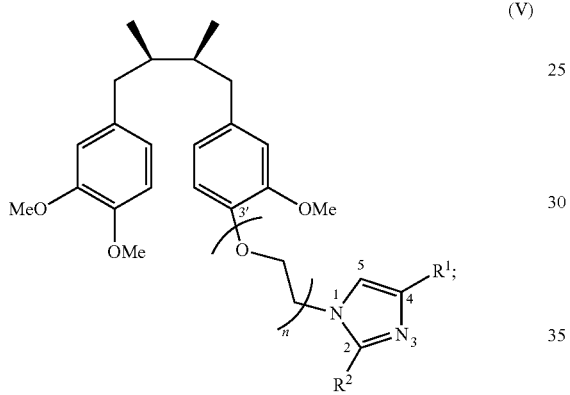

(V)

wherein Y is a polyethylene glycol moiety;
n is 1-10; and
wherein $R^1$ and $R^2$ are different, and are each selected from the group consisting of H and $NO_2$.

7. The compound, salt, solvate, or stereoisomer of claim 6, wherein n=1.

8. The compound, salt, solvate, or stereoisomer of claim 6, wherein n=4.

9. The compound, salt, solvate, or stereoisomer of claim 8, wherein the compound is one of the following:

Compound 10a

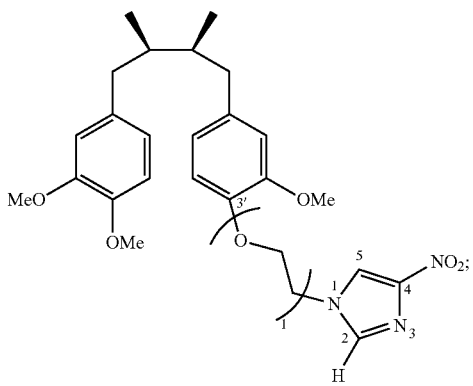

Compound 10b

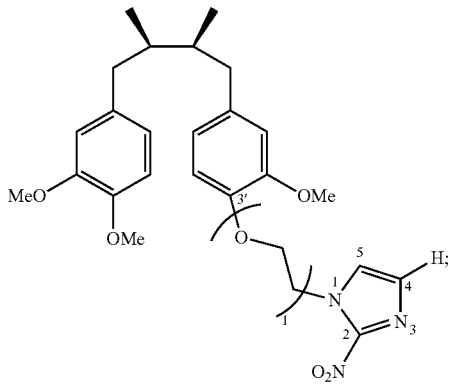

Compound 10c

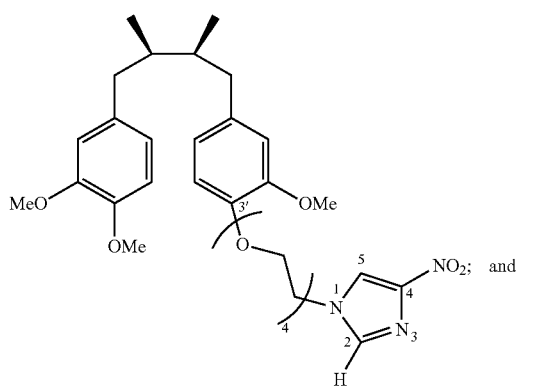

Compound 10d

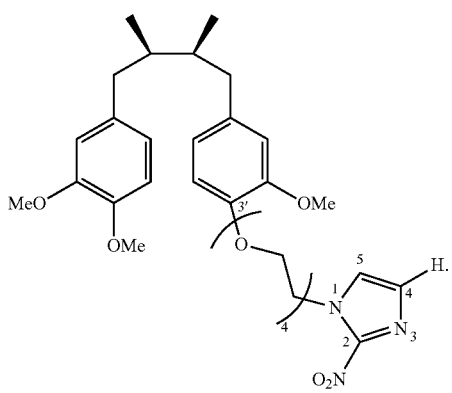

10. A pharmaceutical composition comprising a compound, salt, solvate, or stereoisomer of claim 9, and a pharmaceutically acceptable carrier.

11. A pharmaceutical composition comprising a compound, salt, solvate, or stereoisomer of claim 9, at least one additional therapeutic agent, and a pharmaceutically acceptable carrier.

12. The pharmaceutical composition of claim 11, wherein the additional therapeutic agent is an anticancer agent selected from the group consisting of antimitotics, antineoplastics, antimetabolites, and alkylating agents.

13. The pharmaceutical composition of claim 11, wherein the additional therapeutic agent is an imaging agent.

14. A method of treating cancer in a subject comprising administering to the subject an effective amount of a compound, salt, solvate, or stereoisomer of claim 9.

15. The method of claim 14, wherein the cancer is selected from the group consisting of hepatocellular carcinoma, breast cancer and pancreatic cancer.

16. A compound of Formula II:

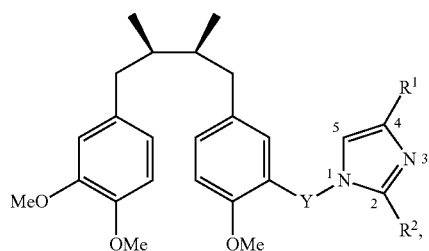

(II)

wherein $R^1$ and $R^2$ are the same or different, and are each selected from the group consisting of H and electron withdrawing groups; and wherein Y is a linking group consisting of a water soluble polymer having n subunits, wherein n is an integer from 1 to 10, and wherein the polymer is selected from the group consisting of polyethylene glycol, polyvinyl alcohol, polycaprolactone, polypropylene glycol, polyethyloxazoline, and poly-L-lactic acid and related synthetic hydrophilic polymers thereof.

17. The compound, salt, solvate, or stereoisomer of claim 16 wherein the compound is a compound of Formula (III):

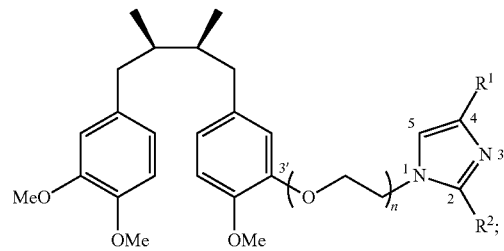

(III)

wherein Y is a polyethylene glycol moiety;

n is 1-10; and wherein $R^1$ and $R^2$ are different, and are each selected from the group consisting of H and $NO_2$.

18. The compound, salt, solvate, or stereoisomer of claim 16, wherein the electron withdrawing group is selected from the group consisting of SCN, $N_3$, CN, $SO_3H$, $B(OH)_2$, $PO(OH)_2$, $SO_2NHOH$, $SO_2NH_2$, CONHOH, $NO_2$, CHO, COOR", COR", $NR"_3+$, wherein R" is H or $C_1$-$C_6$ alkyl, and $CZ_3$, wherein Z is F, Cl, or Br.

19. The compound, salt, solvate, or stereoisomer of claim 18, wherein n=1.

20. The compound, salt, solvate, or stereoisomer of claim 18, wherein n=4.

21. The compound, salt, solvate, or stereoisomer of claim 18, wherein the compound is one of the following:

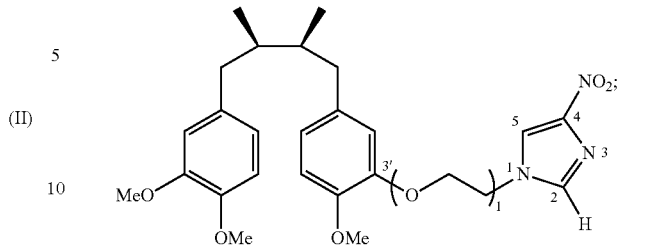

Compound 7a

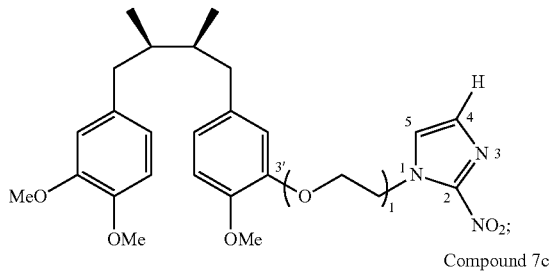

Compound 7b

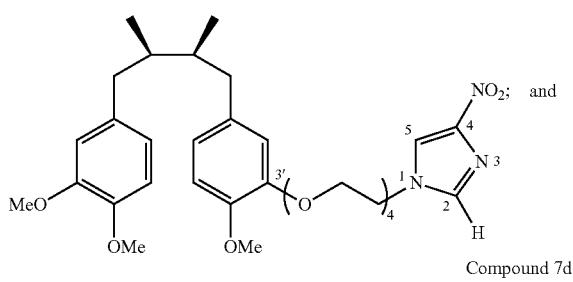

Compound 7c

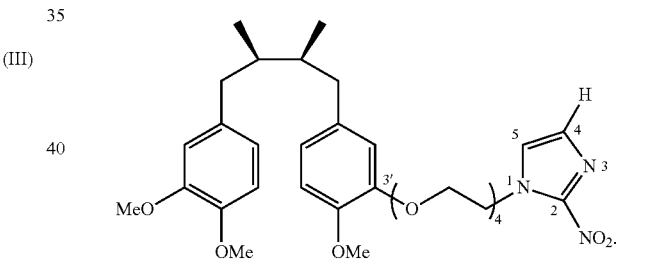

Compound 7d

22. A pharmaceutical composition comprising a compound, salt, solvate, or stereoisomer of claim 21, and a pharmaceutically acceptable carrier.

23. A pharmaceutical composition comprising a compound, salt, solvate, or stereoisomer of claim 21, at least one additional therapeutic agent, and a pharmaceutically acceptable carrier.

24. The pharmaceutical composition of claim 23, wherein the additional therapeutic agent is an anticancer agent selected from the group consisting of antimitotics, antineoplastics, antimetabolites, and alkylating agents.

25. The pharmaceutical composition of claim 23, wherein the additional therapeutic agent is an imaging agent.

26. A method of treating cancer in a subject comprising administering to the subject an effective amount of a compound, salt, solvate, or stereoisomer of claim 21.

27. The method of claim 26, wherein the cancer is selected from the group consisting of hepatocellular carcinoma, breast cancer and pancreatic cancer.

* * * * *